US012639963B2

(12) United States Patent (10) Patent No.: US 12,639,963 B2

Shiraishi (45) Date of Patent: May 26, 2026

(54) INFORMATION PROCESSING APPARATUS, INFORMATION PROCESSING METHOD, AND PROGRAM

(71) Applicant: FUJIFILM CORPORATION, Tokyo (JP)

(72) Inventor: Yasushi Shiraishi, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 243 days.

(21) Appl. No.: 18/534,721

(22) Filed: Dec. 11, 2023

(65) Prior Publication Data

US 2024/0112479 A1    Apr. 4, 2024

Related U.S. Application Data

(63) Continuation of application No. PCT/JP2022/020253, filed on May 13, 2022.

(30) Foreign Application Priority Data

Jun. 24, 2021    (JP) ................................. 2021-104817

(51) Int. Cl.
*G06K 9/00* (2022.01)
*C12M 1/34* (2006.01)
(Continued)

(52) U.S. Cl.
CPC ........... *G06V 20/695* (2022.01); *C12M 41/46* (2013.01); *G06V 10/774* (2022.01); *G06V 20/698* (2022.01); *G16B 20/20* (2019.02)

(58) Field of Classification Search
None
See application file for complete search history.

(56) References Cited

U.S. PATENT DOCUMENTS 10,352,843 B2    7/2019 Nakatsuji et al.
2016/0370569 A1  12/2016 Matsumoto
(Continued)

FOREIGN PATENT DOCUMENTS

WO    2015/133185 A1    9/2015
WO    2016/088243 A1    6/2016
(Continued)

OTHER PUBLICATIONS

Zagar, Lan et al., "Stage prediction of embryonic stem cell differentiation from genome-wide expression data", Bioinformatics, vol. 27, No. 18, Oxford University Press, Sep. 15, 2011, pp. 2546-2553, XP093200438, [retrieved on Aug. 30, 2024].
(Continued)

*Primary Examiner* — SJ Park
(74) *Attorney, Agent, or Firm* — SOLARIS Intellectual Property Group, PLLC

(57) ABSTRACT

An information processing apparatus for predicting a success or failure of differentiation of cells on the basis of a captured image obtained by imaging a cell population cultured in a cell-culture container includes at least one processor. The at least one processor extracts a feature quantity based on an appearance of the cells by performing image processing on the captured image, and predicts the success or failure of differentiation of the cells on the basis of the extracted feature quantity.

17 Claims, 18 Drawing Sheets

(51) Int. Cl.
    *G06V 10/774*      (2022.01)
    *G06V 20/69*       (2022.01)
    *G16B 20/20*       (2019.01)

(56)           References Cited

U.S. PATENT DOCUMENTS

| | | | |
|---|---|---|---|
| 2020/0126234 A1 | 4/2020 | Yokota et al. | |
| 2021/0087517 A1 | 3/2021 | Murakami et al. | |
| 2022/0189149 A1 | 6/2022 | Shiraishi | |
| 2022/0215543 A1* | 7/2022 | Inoue | G16H 40/67 |
| 2022/0244243 A1 | 8/2022 | Murakami et al. | |
| 2022/0253016 A1 | 8/2022 | Murakami et al. | |
| 2022/0396765 A1 | 12/2022 | Murakami et al. | |
| 2023/0123767 A1 | 4/2023 | Kakeda | |
| 2023/0154003 A1 | 5/2023 | Taniguchi et al. | |

FOREIGN PATENT DOCUMENTS

| | | |
|---|---|---|
| WO | 2018/101004 A1 | 6/2018 |
| WO | 2019/163802 A1 | 8/2019 |
| WO | 2019/240008 A1 | 12/2019 |
| WO | 2021/059572 A1 | 4/2021 |
| WO | 2021/085033 A1 | 5/2021 |
| WO | 2021/085034 A1 | 5/2021 |
| WO | 2021/085649 A1 | 5/2021 |
| WO | 2021/145402 A1 | 7/2021 |
| WO | 2022/044167 A1 | 3/2022 |

OTHER PUBLICATIONS

Extended European Search Report dated Sep. 17, 2024, issued in corresponding EP Patent Application No. 22828098.8.

International Search Report issued in International Application No. PCT/JP2022/020253 on Jul. 19, 2022.

Written Opinion of the ISA issued in International Application No. PCT/JP2022/020253 on Jul. 19, 2022.

English language translation of the following: Office action dated Jan. 6, 2026 from the JPO in a Japanese patent application No. 2023-529688 corresponding to the instant patent application.

\* cited by examiner

FREQUENCY

DN

DP

TN

TP

FN  FP

K

FEATURE QUANTITY F

ROC CURVE

1

TRUE POSITIVE RATE TPR=TP/(TP+FN)

AUC

0

0          FALSE POSITIVE RATE FPR=FP/(FP+TN)          1

Figure 14:
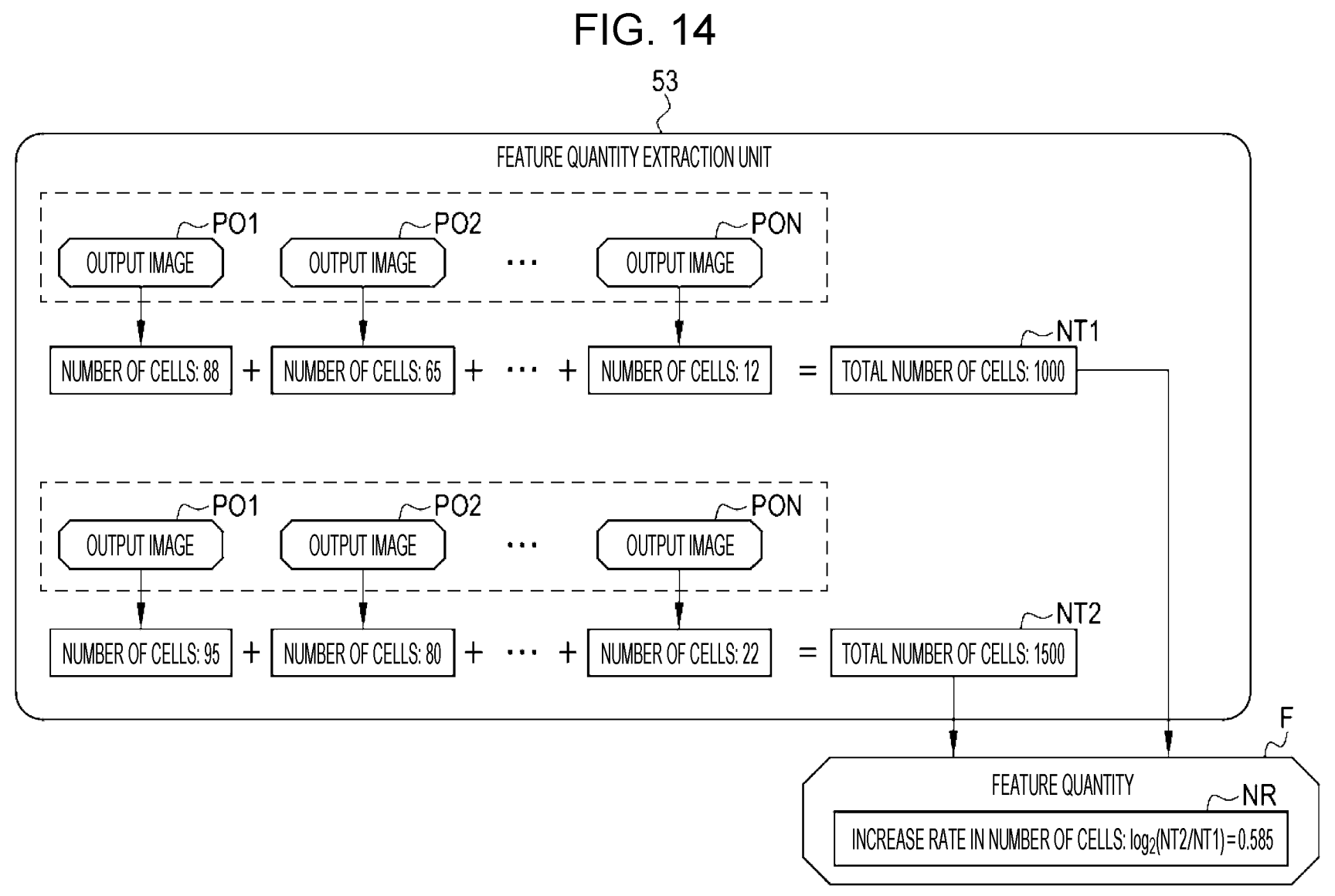

FEATURE QUANTITY EXTRACTION UNIT — 53

PO1   OUTPUT IMAGE    NUMBER OF CELLS: 88

PO2   OUTPUT IMAGE    NUMBER OF CELLS: 65

PON   OUTPUT IMAGE    NUMBER OF CELLS: 12

NT1   TOTAL NUMBER OF CELLS: 1000

PO1   OUTPUT IMAGE    NUMBER OF CELLS: 95

PO2   OUTPUT IMAGE    NUMBER OF CELLS: 80

PON   OUTPUT IMAGE    NUMBER OF CELLS: 22

NT2   TOTAL NUMBER OF CELLS: 1500

F

FEATURE QUANTITY

NR   INCREASE RATE IN NUMBER OF CELLS: $\log_2(NT2/NT1) = 0.585$

Figure 15:
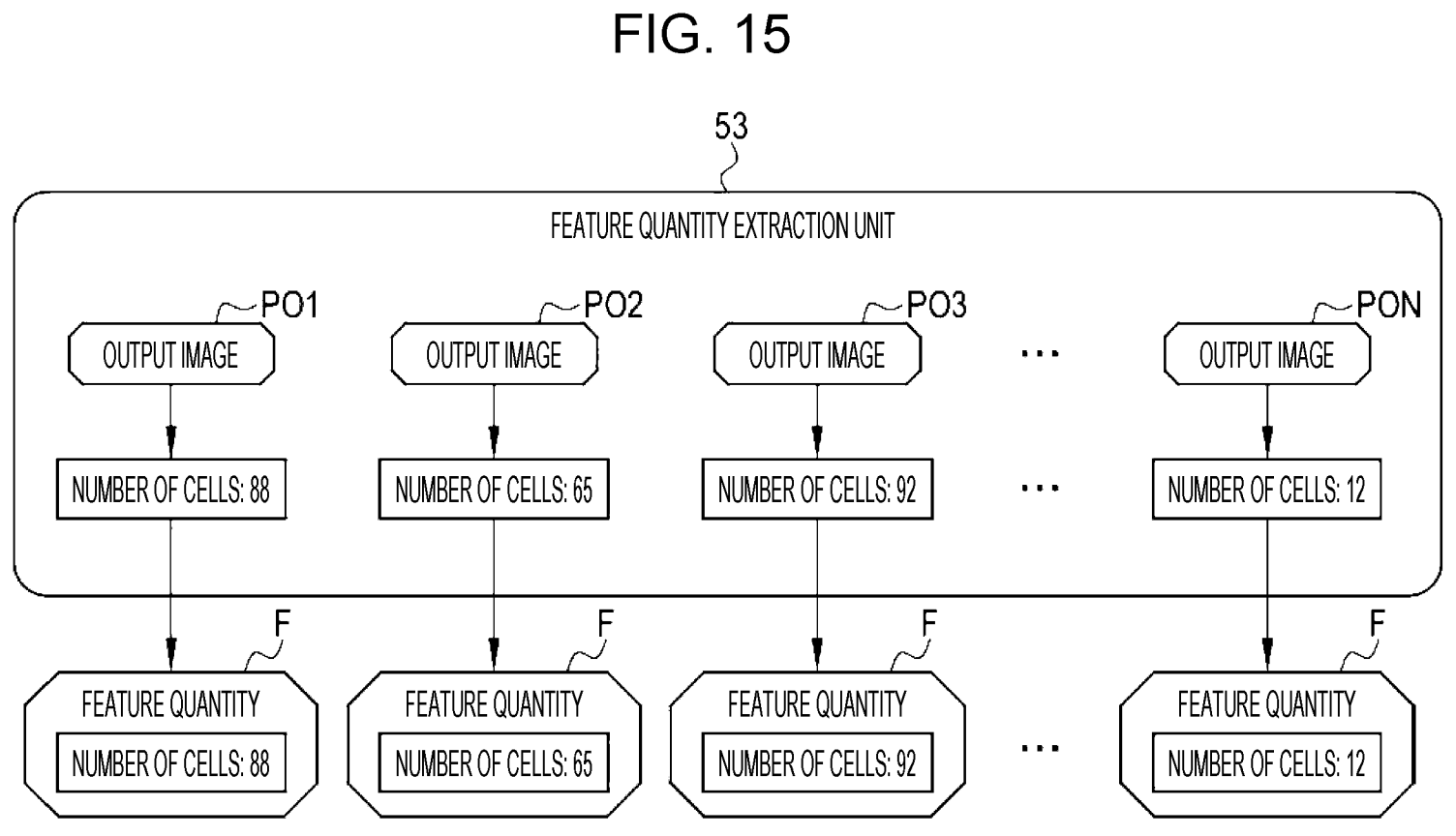

FEATURE QUANTITY EXTRACTION UNIT

PO1

| OUTPUT IMAGE |
| NUMBER OF CELLS: 88 |

F

| FEATURE QUANTITY |
| NUMBER OF CELLS: 88 |

PO2

| OUTPUT IMAGE |
| NUMBER OF CELLS: 65 |

F

| FEATURE QUANTITY |
| NUMBER OF CELLS: 65 |

PO3

| OUTPUT IMAGE |
| NUMBER OF CELLS: 92 |

F

| FEATURE QUANTITY |
| NUMBER OF CELLS: 92 |

PON

| OUTPUT IMAGE |
| NUMBER OF CELLS: 12 |

F

| FEATURE QUANTITY |
| NUMBER OF CELLS: 12 |

FIG. 17

| FEATURE QUANTITY F | AUC | SENSITIVITY | SPECIFICITY |
|---|---|---|---|
| INCREASE RATE IN NUMBER OF CELLS (OVERALL) | 0.963258 | 0.895 | 0.901330 |
| NUMBER OF CELLS (AVERAGE) | 0.948202 | 0.852 | 0.913242 |
| NUCLEUS AREA (AVERAGE) | 0.926246 | 0.895 | 0.816370 |
| N/C RATIO (AVERAGE) | 0.879065 | 0.901 | 0.739733 |
| INCREASE RATE IN NUCLEUS AREA (OVERALL) | 0.760670 | 0.735 | 0.652507 |
| INCREASE RATE OF CIRCULARITY (STANDARD DEVIATION) | 0.733468 | 0.871 | 0.543091 |
| N/C RATIO (STANDARD DEVIATION) | 0.730174 | 0.571 | 0.785161 |
| CIRCULARITY (AVERAGE) | 0.720290 | 0.947 | 0.565687 |
| NUCLEUS AREA (STANDARD DEVIATION) | 0.709930 | 0.819 | 0.524914 |
| INCREASE RATE IN CIRCULARITY (OVERALL) | 0.682057 | 0.956 | 0.534684 |
| INCREASE RATE IN NUMBER OF CELLS (STANDARD DEVIATION) | 0.669572 | 0.946 | 0.506631 |
| INCREASE RATE IN CONFLUENCY (OVERALL) | 0.619209 | 0.918 | 0.414961 |
| INCREASE RATE IN CONFLUENCY (STANDARD DEVIATION) | 0.612424 | 0.816 | 0.391927 |
| INCREASE RATE IN N/C RATIO (OVERALL) | 0.554994 | 0.959 | 0.398812 |
| INCREASE RATE IN NUCLEUS AREA (STANDARD DEVIATION) | 0.552216 | 0.294 | 0.849977 |
| CONFLUENCY (AVERAGE) | 0.548373 | 0.872 | 0.291517 |
| NUMBER OF CELLS (STANDARD DEVIATION) | 0.541288 | 0.296 | 0.789766 |
| INCREASE RATE IN N/C RATIO (STANDARD DEVIATION) | 0.512455 | 0.825 | 0.221272 |
| CONFLUENCY (STANDARD DEVIATION) | 0.510319 | 0.762 | 0.260452 |
| CIRCULARITY (STANDARD DEVIATION) | 0.506512 | 0.907 | 0.251608 |

INFORMATION PROCESSING APPARATUS, INFORMATION PROCESSING METHOD, AND PROGRAM

CROSS-REFERENCE TO RELATED APPLICATIONS

This application is a continuation application of International Application No. PCT/JP2022/020253, filed May 13, 2022, the disclosure of which is incorporated herein by reference in its entirety. Further, this application claims priority from Japanese Patent Application No. 2021-104817, filed on Jun. 24, 2021, the disclosure of which is incorporated herein by reference in its entirety.

BACKGROUND

1. Technical Field

The technique of the present disclosure relates to an information processing apparatus, an information processing method, and a program.

2. Description of the Related Art

Pluripotent stem cells such as induced pluripotent stem (iPS) cells and embryonic stem (ES) cells are cells potentially having an ability to differentiate into various tissues of a living body, and can differentiate into all of the endoderm, the mesoderm, and the ectoderm. The ability of cells to differentiate into different cell types in this manner is called differentiation potency. However, pluripotent stem cells have different differentiation potency from clone to clone, and may fail to differentiate into a specific cell type in some cases. Such unevenness of the differentiation potency becomes apparent only after a differentiation induction process is performed on pluripotent stem cells.

On the other hand, a relatively long period (for example, three months) is required from generation of a pluripotent stem cell to acquisition of cells (hereinafter, referred to as differentiated cells) differentiated into the endoderm, the mesoderm, the ectoderm, or the like. In the production of regenerative medical products derived from pluripotent stem cells, the unevenness of the differentiation potency of the pluripotent stem cells is one factor that markedly reduces the productivity. Therefore, it is considered that if the success or failure of differentiation of stem cells such as pluripotent stem cells can be predicted at a stage before differentiation induction, the productivity and quality of regenerative medical products can be improved.

For example, human-cell-derived intestinal epithelial cells are a drug discovery support product for evaluating absorption of drugs or the like. The production of human-cell-derived intestinal epithelial cells requires a period of about one to two months, and the cost for inducing differentiation of human iPS cells into intestinal epithelial cells is high. Therefore, it is important to detect defective cells before differentiation induction and not to enter the detected defective cells in the next step.

WO2019/240008A discloses a technique for estimating differentiation potency of a pluripotent stem cell before the pluripotent stem cell differentiates into a specific differentiated cell by differentiation induction. Specifically, WO2019/240008A discloses that cell information indicating a state of a cell from production of a pluripotent stem cell to differentiation of the pluripotent stem cell into a specific differentiated cell by differentiation induction and process history information indicating a history of a processing process for obtaining the differentiated cell are acquired, and differentiation potency information indicating differentiation potency of the pluripotent stem cell is derived on the basis of the acquired cell information and process history information.

SUMMARY

However, the technique described in WO2019/240008A requires acquisition of the cell information and the process history information in order to predict the success or failure of differentiation of a cell. The cell information includes appearance information, gene information, secretion information, donor information, or the like. The process history information includes operator information, equipment information, identification information of a culture medium and a reagent, environment information, or the like. As described above, the technique described in WO2019/240008A requires various kinds of information in order to predict the success or failure of differentiation. Thus, development of a simpler prediction method is desired.

The technique of the present disclosure aims to provide an information processing apparatus, an information processing method, and a program that allow the success or failure of differentiation of cells to be easily predicted.

An information processing apparatus according to the present disclosure is an information processing apparatus that predicts a success or failure of differentiation of cells on the basis of a captured image obtained by imaging a cell population cultured in a cell-culture container. The information processing apparatus includes at least one processor configured to extract a feature quantity based on an appearance of the cells by performing image processing on the captured image, and predict the success or failure of differentiation of the cells on the basis of the extracted feature quantity.

Preferably, the at least one processor is configured to predict the success or failure of differentiation of the cells on the basis of only the feature quantity based on the appearance of the cells.

Preferably, the at least one processor is configured to detect cell nuclei from at least one captured image, and extracts information related to the cell nuclei as the feature quantity.

Preferably, the feature quantity includes a number of cells corresponding to a number of cell nuclei, an area of a cell nucleus, an area ratio between a cell nucleus and cytoplasm, or a proportion of a cell-occupied area in the cell-culture container.

Preferably, the feature quantity includes an increase rate in a number of cells calculated on the basis of a plurality of captured images with different image-capturing times.

Preferably, the at least one processor is configured to detect the cell nuclei from the captured image using a trained model obtained by performing machine learning using, as training data, a fluorescence image in which a cell nucleus is stained.

Preferably, the at least one processor is configured to predict the success or failure of differentiation of the cells for each of a plurality of regions into which entirety of the cell-culture container is divided, by using, as the captured image, each of a plurality of region images obtained by imaging the plurality of regions.

Preferably, the at least one processor is configured to calculate a ratio of an area for which differentiation is to be successful to a cell-culture area on the basis of prediction results about the success or failure of differentiation of the cells for the respective regions.

Preferably, the cells are stem cells.

Preferably, the stem cells are in an undifferentiated state.

An information processing method according to the present disclosure is an information processing method for predicting a success or failure of differentiation of cells on the basis of a captured image obtained by imaging a cell population cultured in a cell-culture container. The information processing method includes extracting a feature quantity based on an appearance of the cells by performing image processing on the captured image, and predicting the success or failure of differentiation of the cells on the basis of the extracted feature quantity.

A program according to the present disclosure is a program for causing a computer to execute a process of predicting a success or failure of differentiation of cells on the basis of a captured image obtained by imaging a cell population cultured in a cell-culture container. The process includes extracting a feature quantity based on an appearance of the cells by performing image processing on the captured image, and predicting the success or failure of differentiation of the cells on the basis of the extracted feature quantity.

The technique of the present disclosure can provide an information processing apparatus, an information processing method, and a program that allow the success or failure of differentiation of cells to be easily predicted.

BRIEF DESCRIPTION OF THE DRAWINGS

Exemplary embodiments according to the technique of the present disclosure will be described in detail based on the following figures, wherein:

FIG. 4 is a block diagram illustrating an example of a functional configuration of the information processing apparatus;

FIG. 6 is a diagram illustrating an example of a process performed by a feature quantity extraction unit;

FIG. 10 is a block diagram illustrating an example of a configuration of a training unit;

FIG. 14 is a diagram illustrating an example of a feature quantity extraction process according to the second modification;

FIG. 15 is a diagram illustrating an example of a feature quantity extraction process according to a third modification;

FIG. 17 is a diagram illustrating an example of relationships among various feature quantities, an area under curve (AUC), a sensitivity, and a specificity immediately before differentiation induction;

DETAILED DESCRIPTION

An example of an embodiment according to the technique of the present disclosure will be described with reference to the accompanying drawings.

Figure 1:
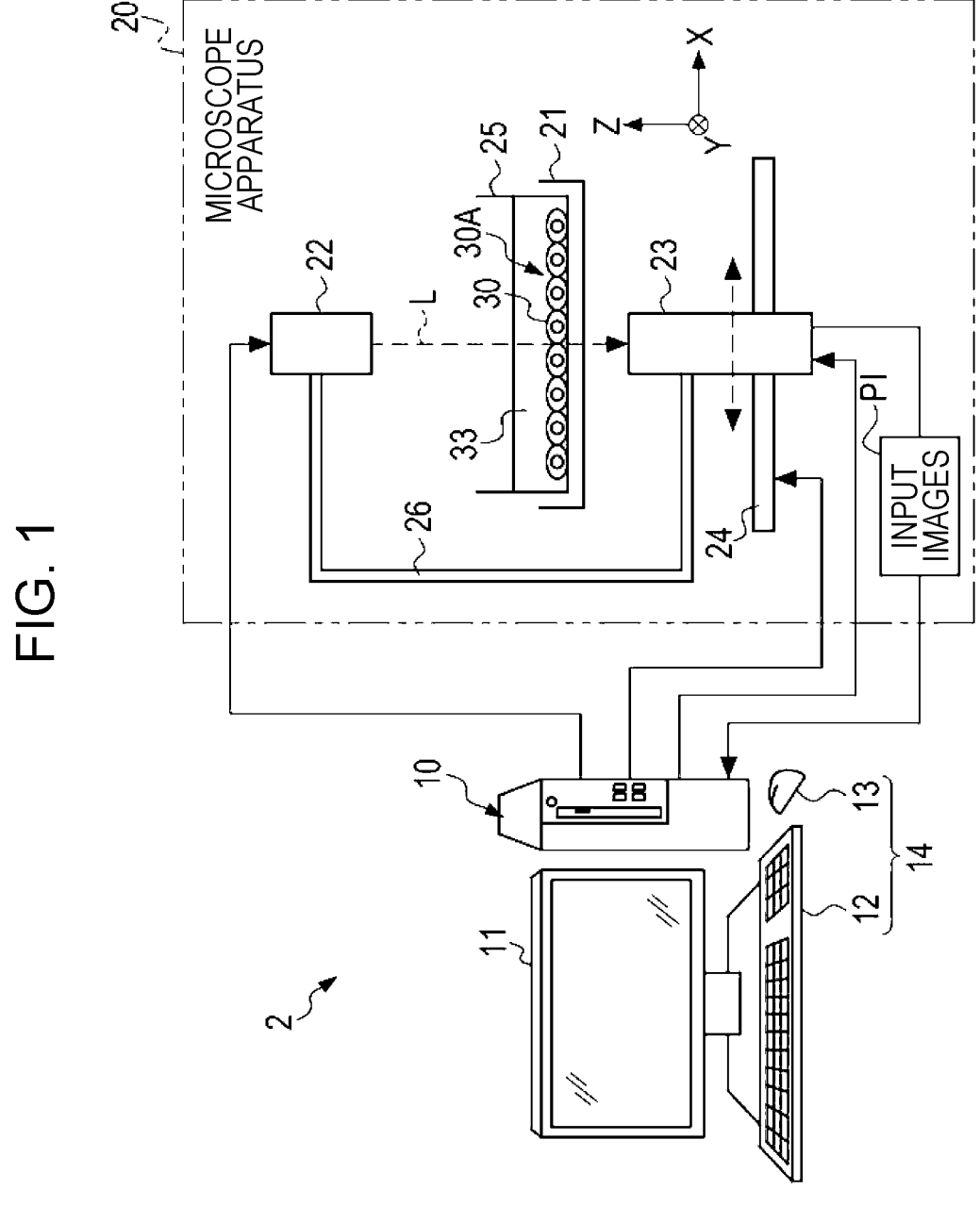
FIG. 1 is a schematic diagram illustrating an example of a configuration of a microscope observation system.

As illustrated in FIG. 1 as an example, a microscope observation system 2 is constituted by an information processing apparatus 10 and a microscope apparatus 20. The information processing apparatus 10 is, for example, a desktop personal computer. A display 11, a keyboard 12, a mouse 13, and the like are connected to the information processing apparatus 10. The keyboard 12 and the mouse 13 constitute an input device 14 with which a user inputs information. The input device 14 includes a touch panel or the like.

The microscope apparatus 20 includes a mount 21, a light source 22, an imaging apparatus 23, and a driving unit 24. The microscope apparatus 20 is a phase contrast microscope or a bright field microscope. A cell-culture container 25 for culturing cells 30 is mounted on the mount 21. The cell-culture container 25 is, for example, a flask. The cells 30 are cultured using a culture medium 33 that fills the cell-culture container 25. The cells 30 are pluripotent stem cells in an undifferentiated state such as iPS cells or ES cells. Note that the cell-culture container 25 is not limited to a flask, and may be a petri dish, a cell-culture dish, a well plate, or the like.

The light source 22 and the imaging apparatus 23 are held by an arm 26. The mount 21 is disposed between the light source 22 and the imaging apparatus 23. Specifically, the light source 22 is disposed above the cell-culture container 25 mounted on the mount 21. The imaging apparatus 23 is disposed at a position below the mount 21 to face the light source 22. The light source 22 emits illumination light L toward the cell-culture container 25. Hereinafter, an emission direction of the illumination light L is referred to as a "Z direction", one direction orthogonal to the Z direction is referred to as an "X direction", and a direction orthogonal to the Z direction and the X direction is referred to as a "Y direction".

The imaging apparatus 23 is, for example, a complementary metal-oxide semiconductor (CMOS) image sensor. The imaging apparatus 23 may be an image sensor provided with color filters or may be a monochrome image sensor. The imaging apparatus 23 images the plurality of cells 30 (also referred to as a cell population 30A) irradiated with the illumination light L by the light sources 22, and outputs captured images obtained as a result of the imaging as input images PI to the information processing apparatus 10.

The driving unit 24 is connected to the imaging apparatus 23 and moves the imaging apparatus 23 in two-dimensional directions. The light source 22 moves in conjunction with movement of the imaging apparatus 23. For example, the driving unit 24 is an XY stage that moves the imaging apparatus 23 in the X direction and the Y direction.

Figure 2:
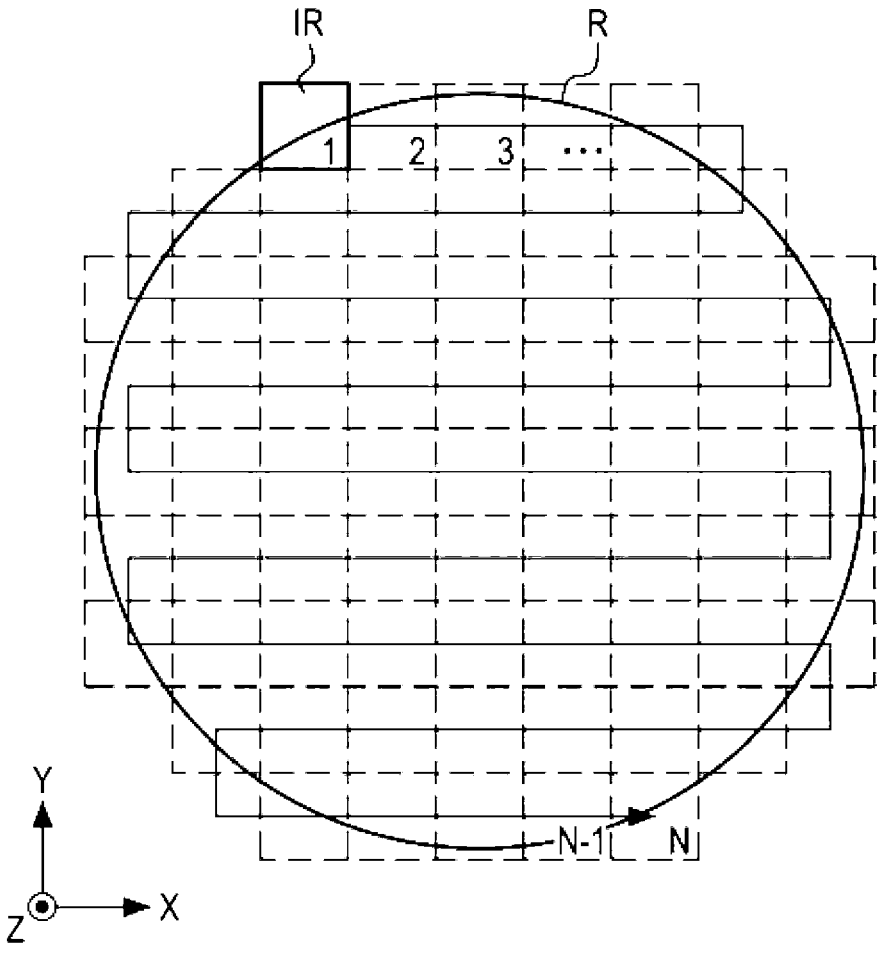
FIG. 2 is a diagram illustrating an example of imaging target ranges.

The information processing apparatus 10 integrally controls operations of the light source 22, the imaging apparatus 23, and the driving unit 24. As illustrated in FIG. 2 as an example, the information processing apparatus 10 controls the driving unit 24 to image the cell population 30A in each imaging target range IR while sequentially changing the imaging target range IR in an imaging region R corresponding to the entirety of the cell-culture container 25. The imaging target ranges IR are regions imaged by the imaging apparatus 23 in one imaging operation. The imaging region R is divided into N imaging target ranges IR. For example, N is several thousands. That is, the microscope apparatus 20 outputs, as an input image PI to the information processing apparatus 10, each of a plurality of region images obtained by imaging a plurality of regions into which the entirety of the cell-culture container 25 is divided. Note that the imaging target ranges IR are an example of "regions" according to the technique of the present disclosure. The input images PI are an example of "captured images" and "region images" according to the technique of the present disclosure.

Figure 3:
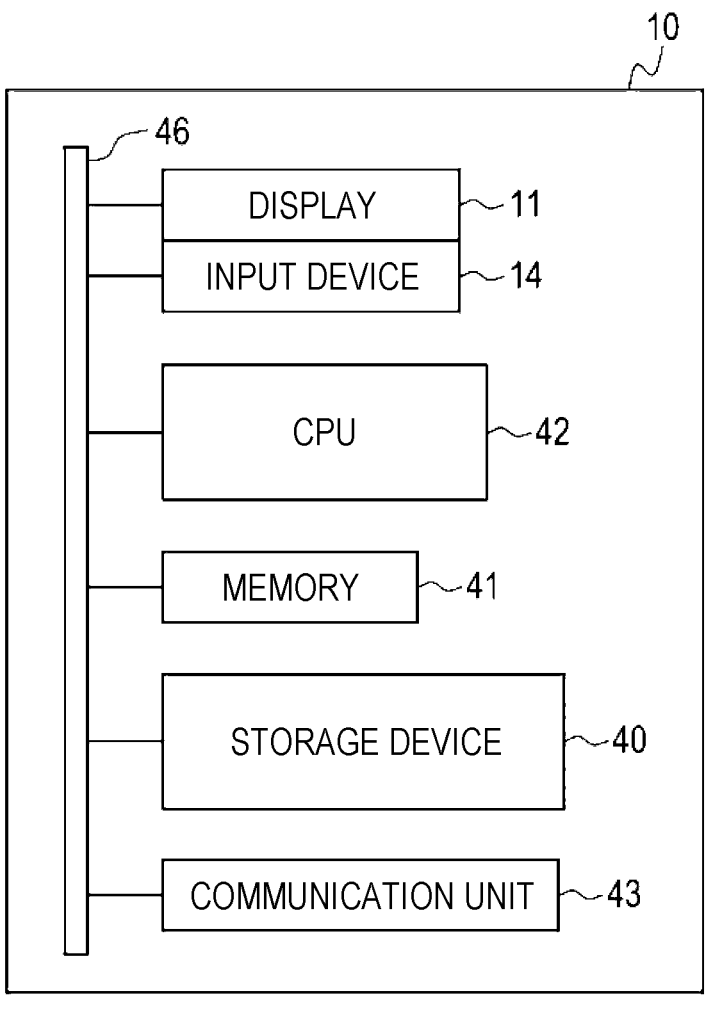
FIG. 3 is a block diagram illustrating an example of an internal configuration of an information processing apparatus.

As illustrated in FIG. 3 as an example, a computer constituting the information processing apparatus 10 includes a storage device 40, a memory 41, a central processing unit (CPU) 42, a communication unit 43, the display 11, and the input device 14. These components are connected to one another through a bus line 46.

The storage device 40 is a hard disk drive built in the computer constituting the information processing apparatus 10 or connected to the computer by a cable or via a network. The storage device 40 may also be a disk array that is a plurality of hard disk drives connected to one another. The storage device 40 stores a control program such as an operating system, various application programs, various kinds of data for these programs, and so on. Note that a solid state drive may be used instead of the hard disk drive.

The memory 41 is a work memory used by the CPU 42 to execute a process. The CPU 42 loads a program stored in the storage device 40 into the memory 41 and executes a process in accordance with the program to integrally control each component of the computer.

The communication unit 43 is a network interface that controls transmission of various kinds of information via a network such as a local area network (LAN). The display 11 displays various screens. The computer constituting the information processing apparatus 10 receives an input of an operation instruction from the input device 14 via the various screens.

The information processing apparatus 10 controls the microscope apparatus 20 to perform so-called time-lapse imaging in which the imaging region R is imaged at regular intervals during culturing of the cell population 30A. On the basis of the input images PI input from the microscope apparatus 20, the information processing apparatus 10 predicts, at a stage before differentiation induction, whether or not differentiation of the cell population 30A is successful (i.e., the success or failure of differentiation of cells) in the case where differentiation induction is performed.

When a regenerative medical product is produced, differentiation induction for causing pluripotent stem cells to differentiate into differentiated cells (germ layer) is performed, so that the pluripotent stem cells usually differentiate into any of the endoderm, the mesoderm, and the ectoderm. However, differentiation potency of the pluripotent stem cells is not uniform, and some cells differentiate into none of the endoderm, the mesoderm, and the ectoderm. In the present embodiment, to improve the productivity and quality of a regenerative medical product, the success or failure of differentiation of cells is predicted at a stage before differentiation induction, and the regenerative medical product is produced using cells of which differentiation is predicted to be successful.

Figure 4:
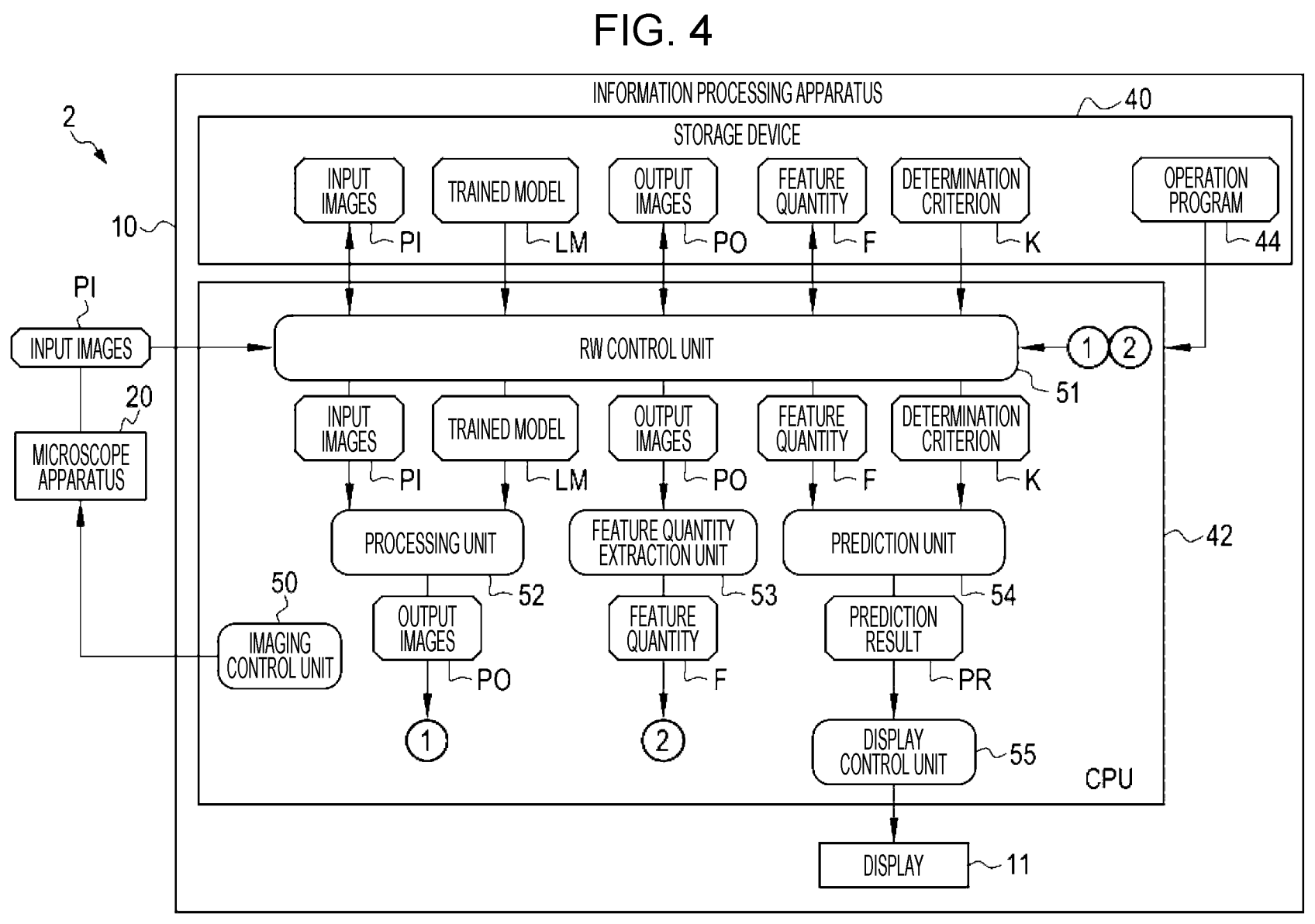

As illustrated in FIG. 4 as an example, the storage device 40 of the information processing apparatus 10 stores an operation program 44. The operation program 44 is an application program for causing the computer to function as the information processing apparatus 10. That is, the operation program 44 is an example of a "program" according to the technique of the present disclosure. In addition to the operation program 44, the storage device 40 stores a trained model LM and a determination criterion K. The storage device 40 also stores the input images PI generated during the operation of the microscope observation system 2, output images PO, and feature quantities F.

In response to the start of the operation program 44, the CPU 42 of the computer constituting the information processing apparatus 10 operates in cooperation with the memory 41 and the like to function as an imaging control unit 50, a read/write (hereinafter abbreviated as RW) control unit 51, a processing unit 52, a feature quantity extraction unit 53, a prediction unit 54, and a display control unit 55.

The imaging control unit 50 controls the microscope apparatus 20 as described above to image the imaging region R representing the entirety of the cell-culture container 25 on an imaging target range IR basis and output a plurality of captured images (input images PI).

The RW control unit 51 controls writing of various kinds of data to the storage device 40 and reading of various kinds of data from the storage device 40. For example, the RW control unit 51 receives the input images PI output from the microscope apparatus 20 and writes the input images PI in the storage device 40. In addition, the RW control unit 51 reads the input images PI and the trained model LM from the storage device 40 and outputs the input images PI and the trained model LM to the processing unit 52. The trained model LM is, for example, a convolutional neural network such as a U-Shaped Neural Network (U-Net), a SegNet, or a Residual Network (ResNet).

The processing unit 52 performs image processing on the input images PI, and outputs the output images PO. Specifically, the processing unit 52 feeds the input image PI to the trained model LM to perform semantic segmentation for identifying a class which is a type of an object depicted in the input image PI in units of pixels. For example, the processing unit 52 classifies each pixel of the input image PI into any of three classes of a cell nucleus, cytoplasm, and a culture medium. Each pixel is labeled to represent the class. The processing unit 52 outputs the image in which each pixel of the input image PI is classified by the trained model LM, as the output image PO to the RW control unit 51. The processing unit 52 generates and outputs the output image PO for each of the plurality of input images PI obtained from one imaging region R. The RW control unit 51 writes the plurality of output images PO output from the processing unit 52 in the storage device 40.

The RW control unit 51 reads the output images PO from the storage device 40, and outputs the output images PO to the feature quantity extraction unit 53. The feature quantity extraction unit 53 extracts the feature quantity F based on an appearance of the cells 30 by using the output images PO. In the present embodiment, the feature quantity extraction unit 53 detects individual cell nuclei from the output image PO, on the basis of the labels attached to the respective pixels of the output image PO, and counts the number of detected cell nuclei to derive the number of cells 30 per unit area (hereinafter, referred to as the number of cells). The feature quantity extraction unit 53 also determines the number of cells for each of the plurality of output images PO, and derives an average number of cells per output image PO. The feature quantity extraction unit 53 outputs the derived average number of cells as the feature quantity F. The RW control unit 51 writes the feature quantity F output from the feature quantity extraction unit 53 in the storage device 40. Note that in the present disclosure, the number of cells means the number of cells 30 per unit area.

The RW control unit 51 reads the feature quantity F and the determination criterion K from the storage device 40, and outputs the feature quantity F and the determination criterion K to the prediction unit 54. The prediction unit 54 predicts the success or failure of differentiation of the cell population 30A on the basis of the feature quantity F and the determination criterion K. If the feature quantity F (i.e., the average number of cells) is greater than or equal to the determination criterion K, the prediction unit 54 predicts that differentiation is to be successful. On the other hand, if the feature quantity F is less than the determination criterion K, the prediction unit 54 predicts that differentiation is to be unsuccessful. The prediction unit 54 outputs a prediction result PR about the success or failure of differentiation of the cell population 30A to the display control unit 55.

The display control unit 55 controls display of various screens on the display 11. The display control unit 55 displays the prediction result PR obtained by the prediction unit 54 on the display 11. Note that the display control unit 55 may cause the display 11 to display the feature quantity F and the output image PO together with the prediction result PR.

Figure 5:
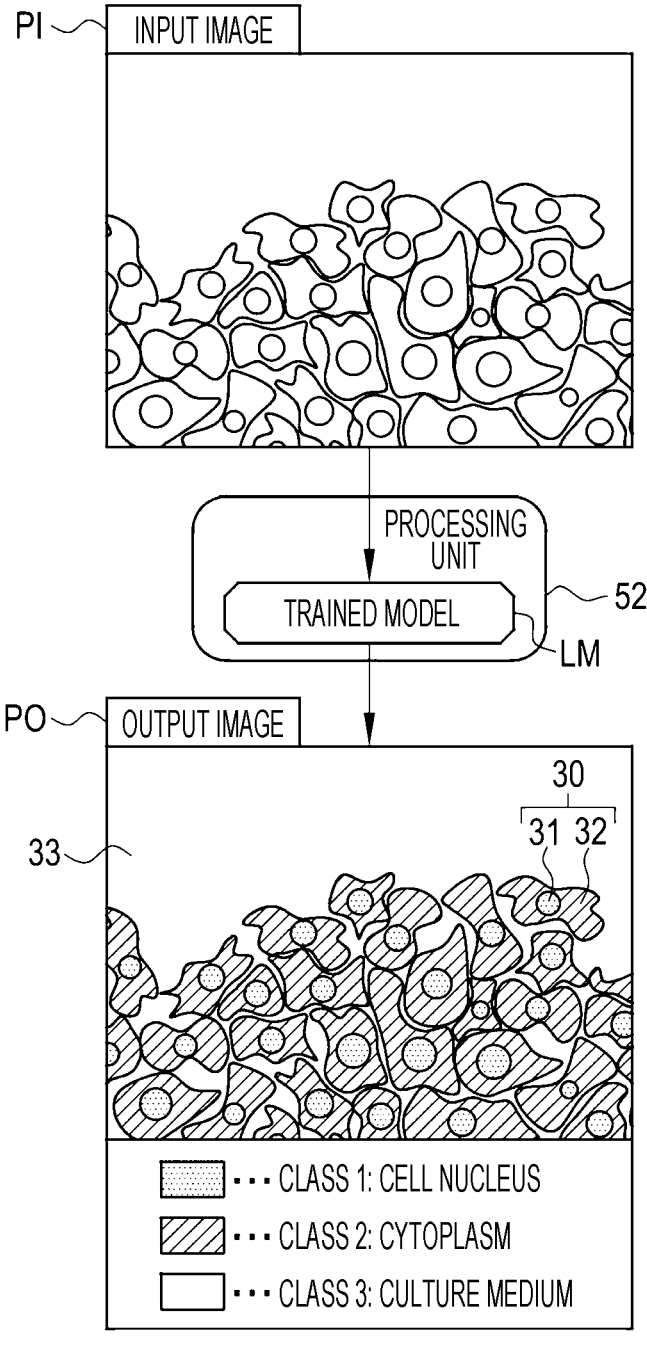
FIG. 5 is a diagram illustrating an example of a process performed by a processing unit.

As illustrated in FIG. 5 as an example, the processing unit 52 feeds the input image PI to the trained model LM to generate the output image PO. The output image PO is an image in which cell nuclei 31 classified into a class 1, cytoplasm 32 classified into a class 2, and the culture medium 33 classified into a class 3 are colored differently. The cell 30 is constituted by the cell nucleus 31 and the cytoplasm 32 corresponding to each other.

In the present embodiment, the feature quantity extraction unit 53 extracts information related to the cell nuclei 31 as the feature quantity F. More specifically, as the information related to the cell nuclei 31, the feature quantity extraction unit 53 extracts the number of cells corresponding to the number of cell nuclei 31 as the feature quantity F.

Figure 6:
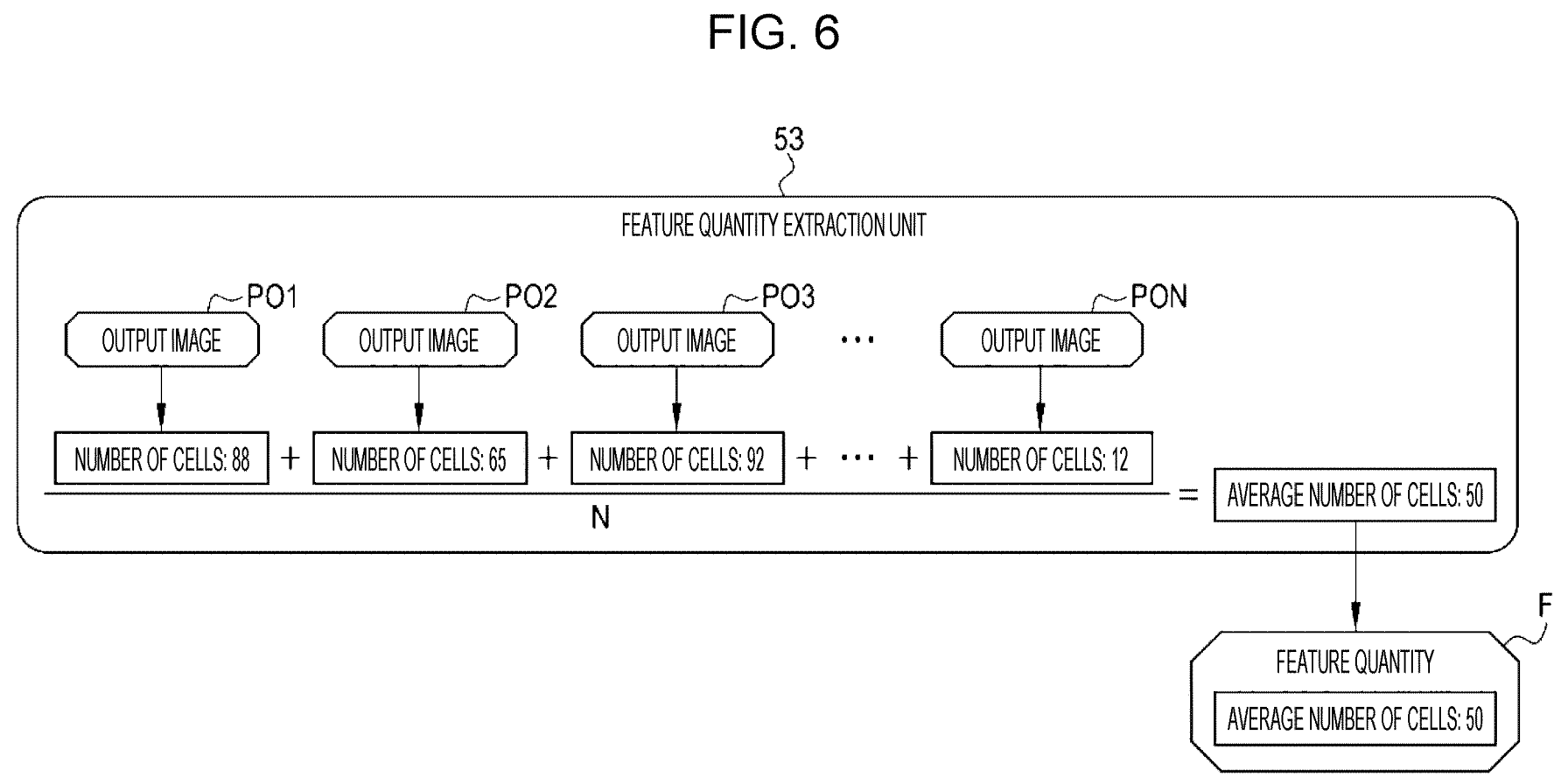

As illustrated in FIG. 6 as an example, the feature quantity extraction unit 53 counts the number of cells for each of a plurality of output images PO1 to PON corresponding to the plurality of imaging target ranges IR illustrated in FIG. 2. Note that an output image POn represents the output image PO corresponding to an n-th imaging target range IR. Here, n=1, 2, 3, . . . N. The feature quantity extraction unit 53 determines the sum of the numbers of cells in the plurality of output images PO1 to PON, and divides the sum of the numbers of cells by N to derive the average number of cells.

Figures 7, 8:
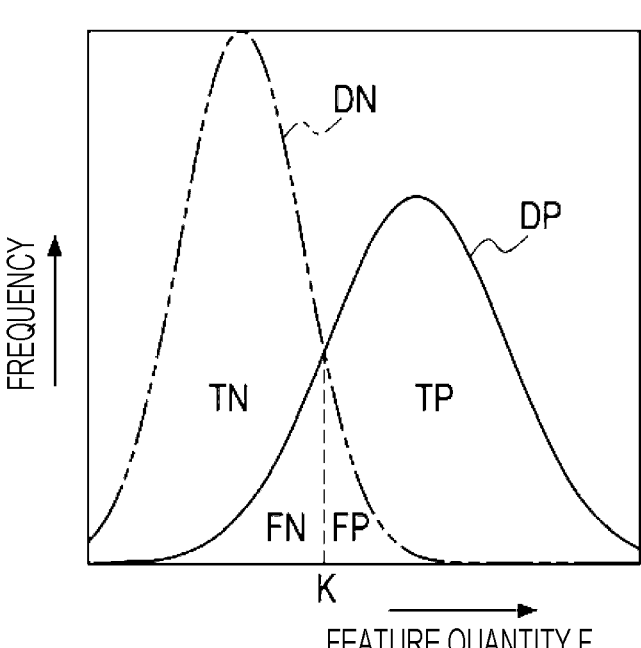
FIG. 7 is a diagram illustrating an example of a determination criterion determining method.
FIG. 8 is a diagram illustrating an example of a receiver operating characteristic (ROC) curve.

As illustrated in FIG. 7 as an example, the determination criterion K used by the prediction unit 54 is a value determined on the basis of a result of a past cell culture test. In FIG. 7, DP represents a distribution of a cell population of which differentiation by differentiation induction is successful in the past cell culture test with respect to the feature quantity F. DN represents a distribution of a cell population of which differentiation by differentiation induction is unsuccessful in the past cell culture test with respect to the feature quantity F. For example, the determination criterion K is set at a boundary value where the distribution DP and the distribution DN intersect with each other. The determination criterion K is a so-called cutoff value.

In FIG. 7, TP represents the number of true positives that is the number of cell populations included in a region where the distribution DP is greater than or equal to the determination criterion K. TN represents the number of true negatives that is the number of cell populations included in a region where the distribution DN is less than the determination criterion K. FN represents the number of false negatives that is the number of cell populations included in a region where the distribution DP is less than the determination criterion K. FP represents the number of false positives that is the number of cell populations included in a region where the distribution DN is greater than or equal to the determination criterion K.

FIG. 8 illustrates an example of a receiver operating characteristic (ROC) curve determined on the basis of a true positive rate and a false positive rate. The ROC curve is a curve representing a relationship between the true positive rate (TPR) and the false positive rate (FPR) in the case where the determination criterion K is changed. The true positive rate is also referred to as a sensitivity. The true positive rate TPR is calculated by $TPR=TP/(TP+FN)$. The false positive rate FPR is calculated by $FPR=FP/(FP+TN)$.

An area under the curve (AUC), which is an area of a region below the ROC curve, represents a prediction accuracy of prediction about differentiation of cells performed on the basis of the feature quantity F. The AUC takes a value of 0 or greater and less than 1. The AUC closer to 1 indicates a higher accuracy in prediction of differentiation of cells. The applicant has confirmed that when the average number of cells is used as the feature quantity F, the AUC is equal to "0.948202", which is close to 1 and thus the high prediction accuracy is realized.

A differentiation prediction process performed by the information processing apparatus 10 will be described next with reference to a flowchart illustrated in FIG. 9 as an example. First, in the information processing apparatus 10, the CPU 42 executes a process on the basis of the operation program 44, so that the CPU 42 functions as the imaging control unit 50, the RW control unit 51, the processing unit 52, the feature quantity extraction unit 53, the prediction unit 54, and the display control unit 55 as illustrated in FIG. 4.

Figure 9:
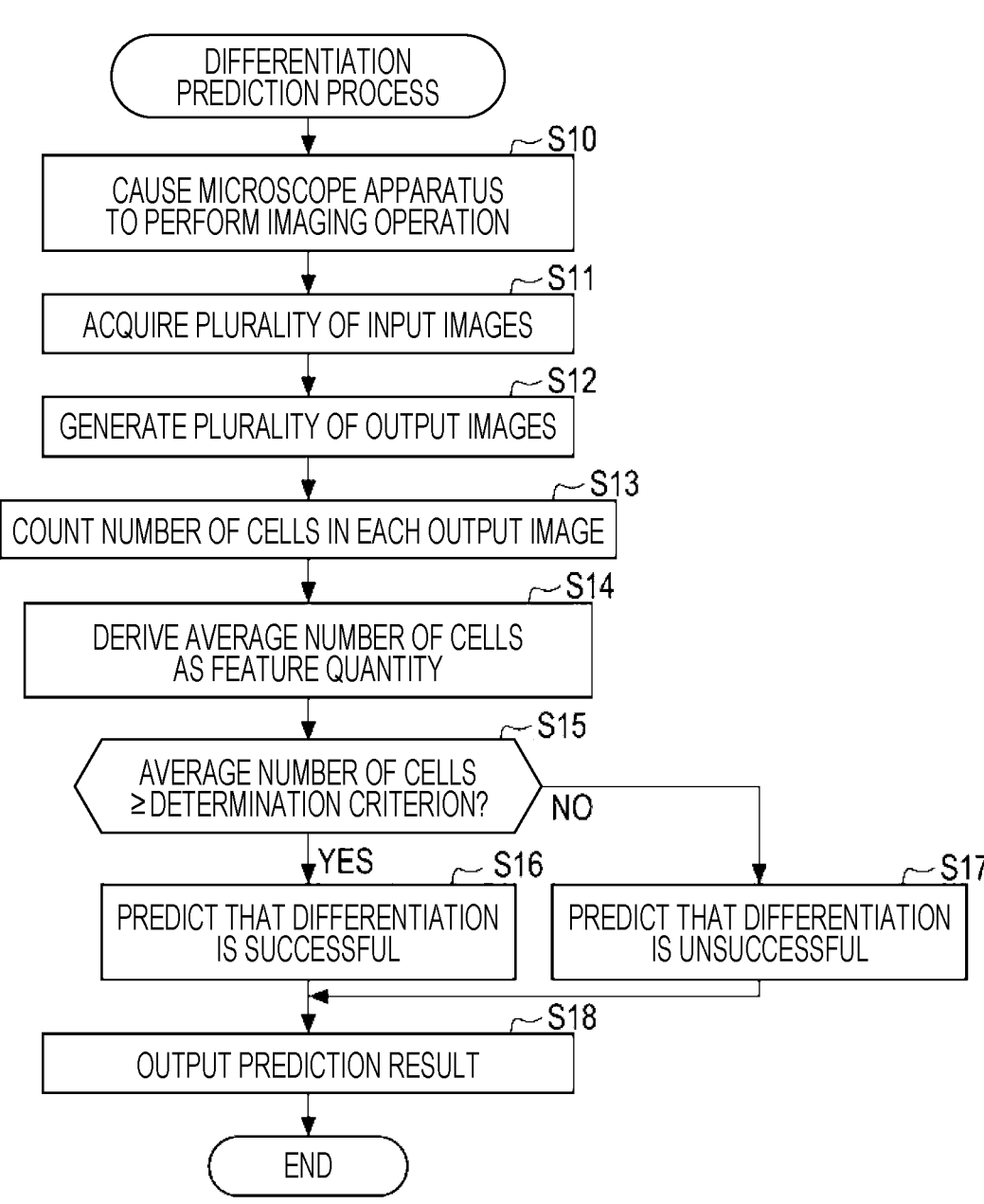
FIG. 9 is a flowchart illustrating an example of a flow of a differentiation prediction process.

As illustrated in FIG. 9, the imaging control unit 50 controls the microscope apparatus 20 to image the imaging region R illustrated in FIG. 2 on the imaging target range IR basis and outputs N captured images (input images PI) (step S10). The information processing apparatus 10 acquires the N input images PI output from the microscope apparatus 20, and writes the N input images PI in the storage devices 40 via the RW control unit 51 (step S11). The N input images PI written in the storage device 40 are read and output to the processing unit 52 by the RW control unit 51.

The processing unit 52 sequentially inputs the N input images PI to the trained model LM, and generates and outputs N output images PO (step S12). The N output images PO output from the processing unit 52 are written in the storage device 40 via the RW control unit 51. The N output images PO written in the storage device 40 are read and output to the feature quantity extraction unit 53 by the RW control unit 51.

The feature quantity extraction unit 53 counts the number of cells for each of the N output images PO (step S13). The feature quantity extraction unit 53 then divides the sum of the numbers of cells by N to derive the average number of cells per output image PO (step S14). The feature quantity extraction unit 53 outputs the average number of cells as the feature quantity F. The feature quantity F output from the feature quantity extraction unit 53 is written in the storage device 40 via the RW control unit 51. The feature quantity F written in the storage device 40 is read and output to the prediction unit 54 by the RW control unit 51.

The prediction unit 54 determines whether the average number of cells, which is the feature quantity F, is greater than or equal to the determination criterion K (step S15). If the average number of cells is greater than or equal to the determination criterion K (step S15: YES), the prediction unit 54 predicts that differentiation of the cell population 30A is to be successful (step S16). On the other hand, if the average number of cells is less than the determination criterion K (step S15: NO), the prediction unit 54 predicts that differentiation of the cell population 30A is to be unsuccessful (step S17).

The prediction unit 54 then outputs the prediction result PR obtained in step S16 or step S17 (step S18). The display control unit 55 displays the prediction result PR on the display 11. The sequence of the differentiation prediction process then ends.

Figure 10:
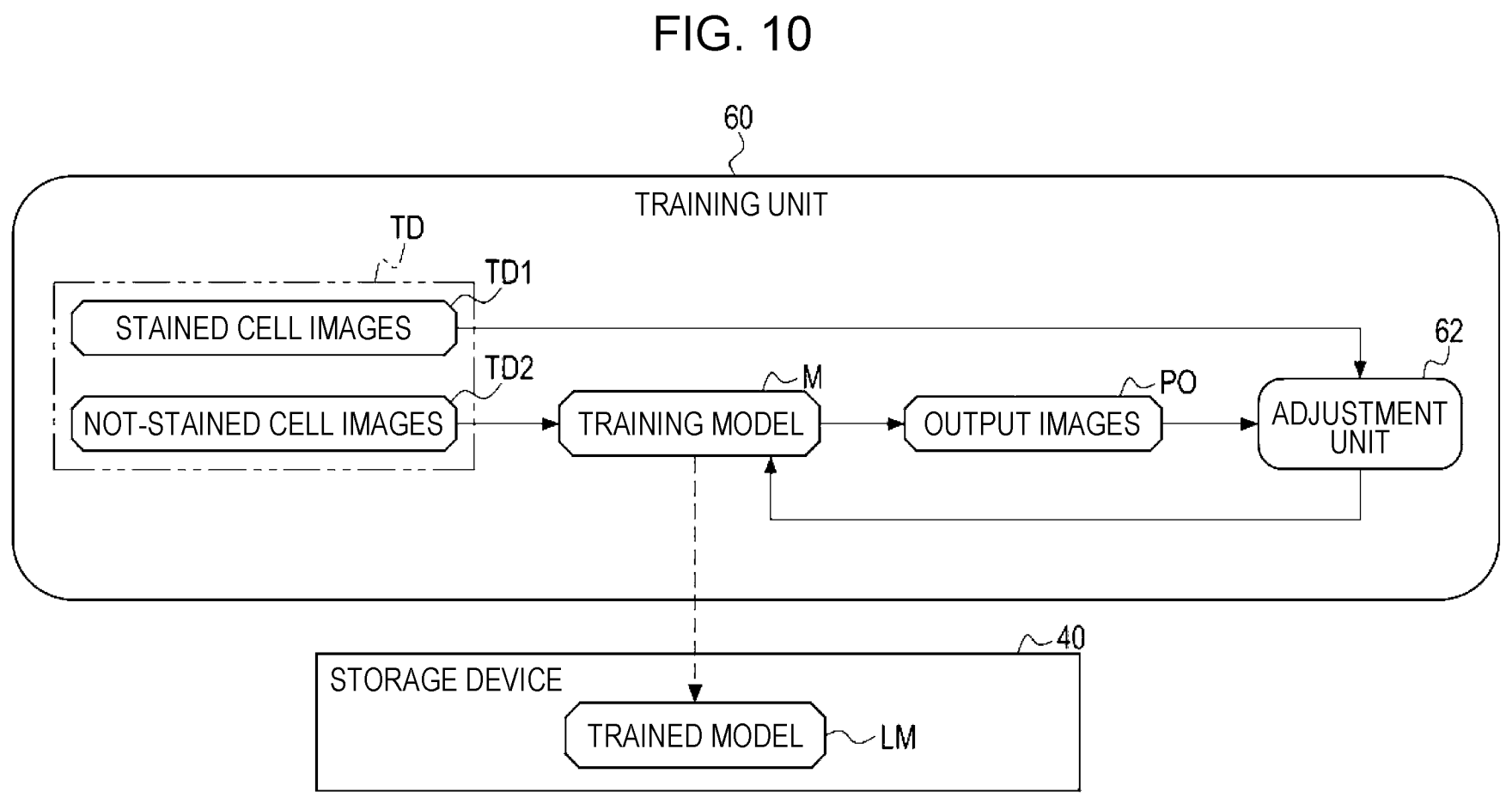

The trained model LM used by the processing unit 52 is created by machine learning using training data in a training phase. As illustrated in FIG. 10 as an example, in the training phase, the CPU 42 executes a process on the basis of the operation program 44, so that the CPU 42 functions as a training unit 60. The training unit 60 includes an adjustment unit 62.

Training data TD is constituted by stained cell images TD1 that are fluorescence images obtained by staining cell nuclei, and not-stained cell images TD2 that are obtained by achromatizing the stained cell images TD1. The stained cell images TD1 are annotation images in which a ground truth label (in the present embodiment, a label indicating one of the classes 1 to 3) is assigned to each pixel.

The training unit 60 inputs the not-stained cell image TD2 as the input image M and causes the training model M to output the output image PO. The training unit 60 inputs the output image PO output from the training model M and the stained cell image TD1 to the adjustment unit 62.

The adjustment unit 62 compares the output image PO with the stained cell image TD1 to evaluate a class determination accuracy. Specifically, the adjustment unit 62 evaluates the class determination accuracy of the training model M by using a loss function. On the basis of an evaluation result, the adjustment unit 62 also adjusts values of various parameters of the training model M by using a stochastic gradient descent method or the like.

The training unit 60 repeats input of the not-stained cell image TD2 to the training model M, evaluation of the output image PO and the stained cell image TD1 by the adjustment unit 62, and adjustment of the training model M by using the plurality of pieces of training data TD. The training unit 60 writes the training model M as the trained model LM in the storage device 40 via the RW control unit 51 when the class determination accuracy of the training model M reaches a preset level.

In the above-described differentiation prediction process that is an operation phase, the processing unit 52 generates the output image PO by using the trained model LM on which machine learning has been performed by the training unit 60.

Processes performed by the microscope observation system 2 until differentiated cells (germ layers) such as the endoderm, the mesoderm, and the ectoderm are obtained from pluripotent stem cells will be described next.

Figure 11:
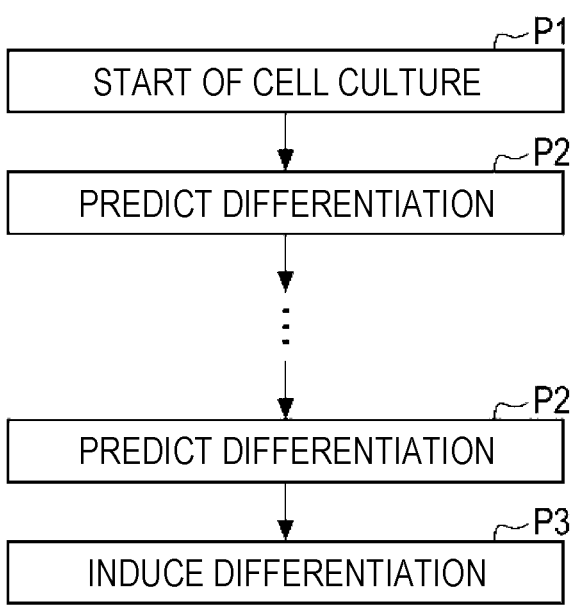
FIG. 11 is a diagram illustrating an example of processes performed to obtain differentiated cells from pluripotent stem cells.

As illustrated in FIG. 11 as an example, in a first process P1, for example, expansion culture for proliferating pluripotent stem cells generated from somatic cells collected from a living body is started. When iPS cells are used as the pluripotent stem cells, the pluripotent stem cells are generated by, for example, performing a process of introducing reprogramming factors (Oct3/4, Sox2, c-Myc, and Klf4) into somatic cells using episomal plasmids. In the first process P1, for example, expansion culture is performed using an adherent cell culture method in which cells are cultured on the cell-culture container 25. In the expansion culture, a culture medium replacement process for replacing a culture medium in use with a fresh culture medium is performed at an appropriate timing during a culture period. In addition, as the cells grow, processing (passaging processing) of peeling and collecting the cells and seeding the cells again in a new flask is performed. The expansion culture is not limited to adherent cell culture, and a suspension cell culture method using a spinner flask or the like can also be adopted.

After culturing of cells is started in the first process P1, the information processing apparatus 10 performs the above-described differentiation prediction process as a second process P2 during the culture period. The second process P2 is performed periodically (for example, every day). The second process P2 is performed at least immediately before differentiation induction that is a third process P3. If it is predicted in the second process P2 that differentiation is to be unsuccessful, the culture is stopped and the cell population 30A that is cultured in the cell-culture container 25 is not entered to the third process P3.

In the third process P3, differentiation induction for causing the pluripotent stem cells to differentiate into differentiated cells is performed. In the third process P3, for example, processing of adding a differentiation inducer to the pluripotent stem cells is performed. As the differentiation inducer, various growth factors/cytokines such as FGF-2, Activin, and BMP-4, or various signal inhibitors such as a BMP signal inhibitor and a Wnt signal inhibitor are used. Through the processes described above, the pluripotent stem cells usually differentiate into any of the endoderm, the mesoderm, and the ectoderm.

As described above, the information processing apparatus 10 extracts a feature quantity based on an appearance of cells by performing image processing on a captured image obtained by imaging a cell population cultured in a cell-culture container, and predicts the success or failure of differentiation of the cells on the basis of the extracted feature quantity before differentiation induction, and thus can improve the productivity and quality of a regenerative medical product. In addition, the information processing apparatus 10 predicts the success or failure of differentiation of the cells on the basis of only the appearance of the cells without using gene information, process history information, or the like as in the related art, the success or failure of differentiation of the cells can be simply predicted.

Various modifications of the embodiment described above will be described below.

First Modification

In the embodiment described above, the processing unit 52 classifies each pixel of the input image PI into any of three classes, i.e., the cell nucleus, the cytoplasm, and the culture medium by using the trained model LM but may classify each pixel into any of four classes additionally including a "central region of the cell nucleus" located at the center of the cell nucleus.

Figure 12:
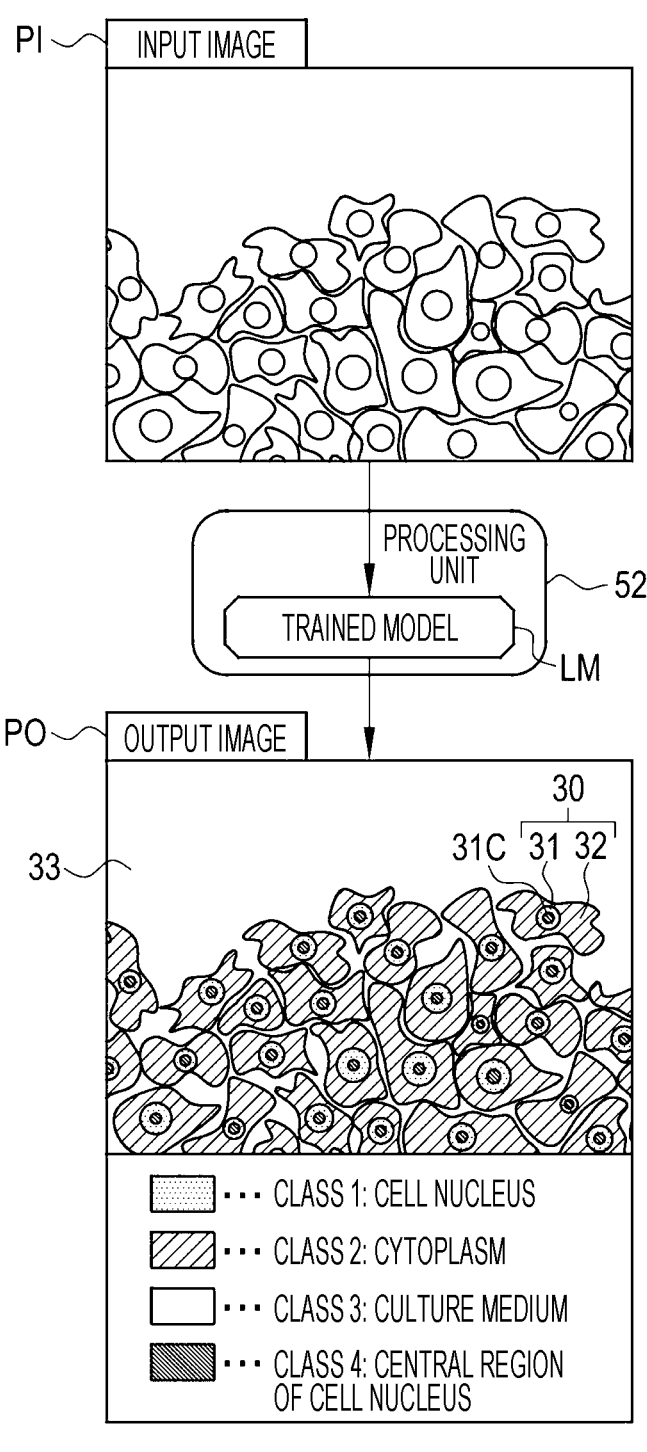
FIG. 12 is a diagram illustrating an example of a process according to a first modification.

As illustrated in FIG. 12 as an example, in a first modification, the output image PO is an image in which the cell nuclei 31 classified into the class 1, the cytoplasm 32 classified into the class 2, the culture medium 33 classified into the class 3, and central regions 31C of the cell nuclei 31 classified into a class 4 are colored differently. In the present modification, the feature quantity extraction unit 53 counts the number of cells from the output image PO on the basis of the central regions 31C of the cells classified into the class 4.

The cell nucleus 31 may be depicted in the output image PO in a state in which the cell nucleus 31 overlaps the cell nucleus 31 of the adjacent cell 30. When two overlapping cell nuclei 31 are depicted in this manner, the feature quantity extraction unit 53 may recognize the two cell nuclei 31 as one cell nucleus 31 and erroneously count the number of cells. The feature quantity extraction unit 53 can count the number of cells more accurately by counting the number of cells on the basis of the central regions 31C smaller than the cell nuclei 31.

Second Modification

In the embodiment described above, the feature quantity F is extracted on the basis of a plurality of captured images (input images PI) with the same image-capturing time. Note that the plurality of captured images with the same image-capturing time refers to a plurality of captured images obtained by an image-capturing sequence performed on one imaging region R. In a second modification, the feature quantity F is extracted on the basis of a plurality of captured images with different image-capturing times. In the present modification, an increase rate in the number of cells is used as the feature quantity F.

Figure 13:
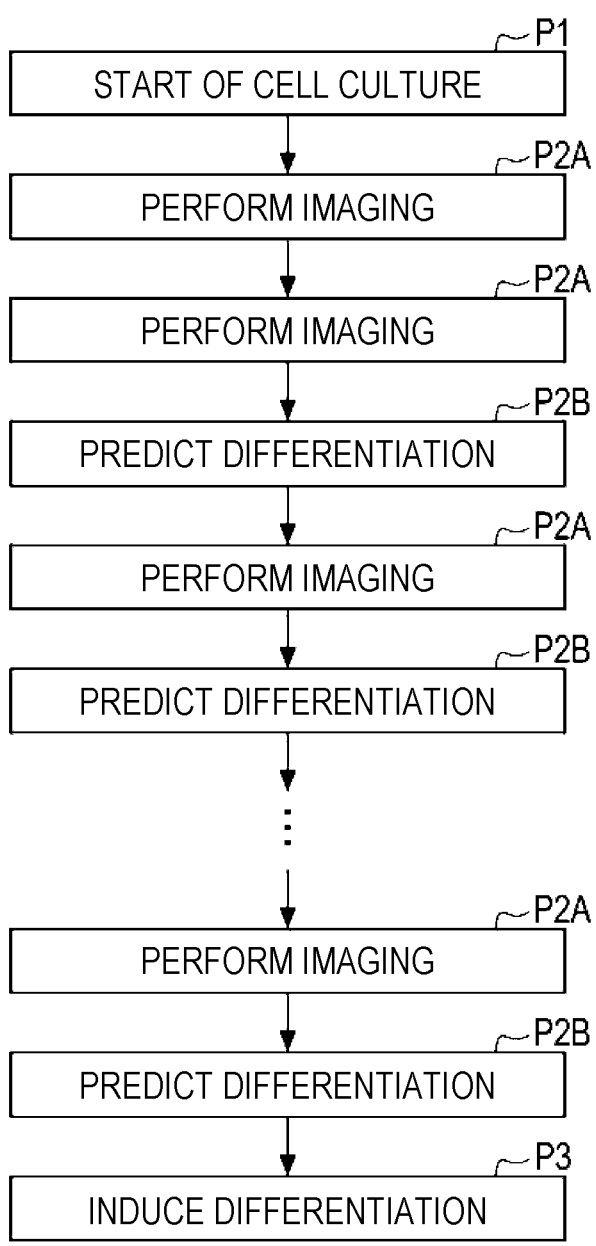
FIG. 13 is a diagram illustrating an example of processes according to a second modification.

As illustrated in FIG. 13 as an example, in the present modification, after culturing of cells is started in the first process P1, a second-A process P2A of imaging the imaging region R with the microscope apparatus 20 is performed during the culture period. The second-A process P2A is performed periodically (for example, every day). In the second-A process P2A, N input images PI are obtained.

In the present modification, after the second-A process P2A is performed twice, a second-B process P2B of performing differentiation prediction is performed every time the second-A process P2A is performed once. In the second-B process P2B, the increase rate in the number of cells is calculated as the feature quantity F on the basis of 2N input images PI obtained in the two most recent second-A processes P2A. In the second-B process P2B, differentiation prediction is performed on the basis of the increase rate in the number of cells. The second-B process P2B is performed at least immediately before differentiation induction that is the third process P3.

As illustrated in FIG. 14 as an example, in the present modification, the feature quantity extraction unit 53 determines the increase rate in the number of cells on the basis of two sets of output images PO1 to PON with different image-capturing times. Specifically, the feature quantity extraction unit 53 calculates a total number of cells NT1 on the basis of the output images PO1 to PON corresponding to the N input images PI acquired at a first image-capturing time, and calculates a total number of cells NT2 on the basis of the output images PO1 to PON corresponding to the N input images PI acquired at a second image-capturing time.

The feature quantity extraction unit 53 then determines an increase rate NR of the cells on the basis of a relational expression $NR=\log_2(NT2/NT1)$, for example.

Third Modification

In the embodiment described above, the information processing apparatus 10 predicts the success or failure of differentiation of cells for the entirety of the imaging region R. In a third modification, the information processing apparatus 10 predicts the success or failure of differentiation of cells for each imaging target range IR. That is, in the present modification, the success or failure of differentiation of cells is predicted for each region on the basis of each of a plurality of region images obtained by imaging a plurality of regions into which the entirety of a cell-culture container is divided.

As illustrated in FIG. 15 as an example, in the present modification, the feature quantity extraction unit 53 extracts the feature quantity F from each of the output images PO1 to PON. In the example illustrated in FIG. 15, the feature quantity extraction unit 53 determines the number of cells from each of the output images PO1 to PON, and uses each number of cells as the feature quantity F. In the present modification, the prediction unit 54 predicts the success or failure of differentiation of cells for each imaging target range IR on the basis of the corresponding feature quantity F.

Figure 16:
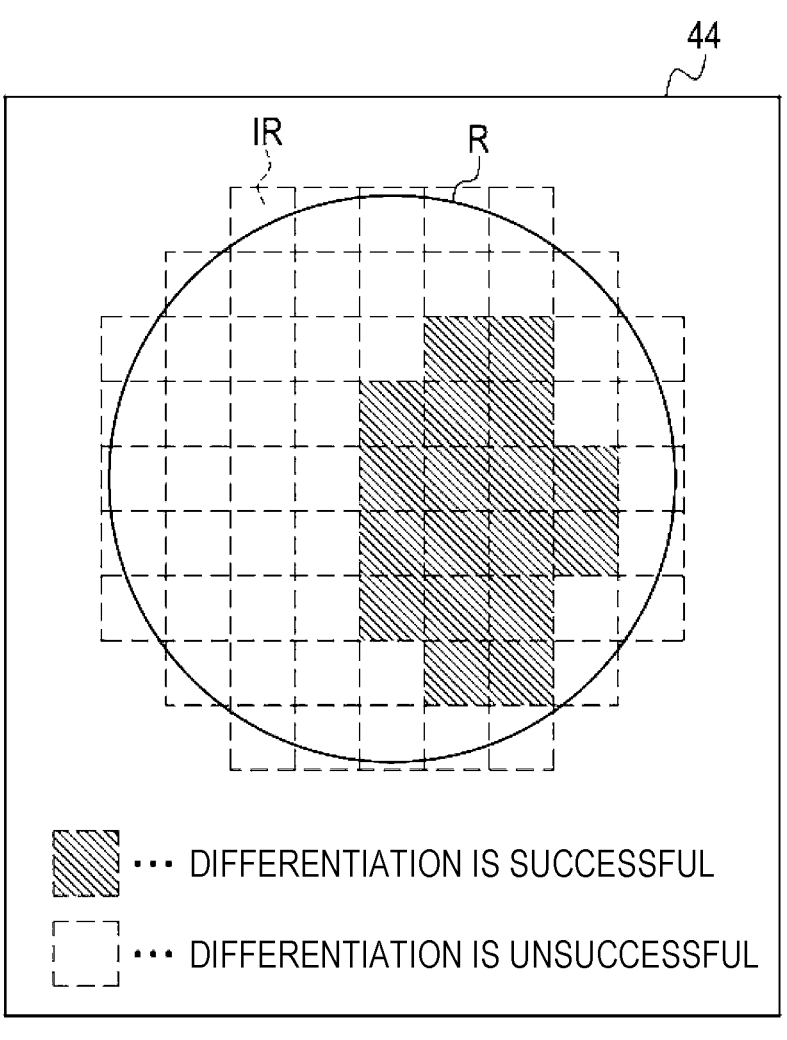
FIG. 16 is a diagram illustrating a display example of a prediction result according to the third modification.

As illustrated in FIG. 16 as an example, in the present modification, the display control unit 55 displays the prediction result PR obtained by the prediction unit 54 on the display 11 for each imaging target range IR. This allows the user to distinguish between regions in which differentiation of cells is predicted to be successful and regions in which differentiation is predicted to be unsuccessful in the cell-culture container 25.

The prediction unit 54 may calculate a ratio of an area for which differentiation is successful to a cell-culture area (i.e., an area of the imaging region R) on the basis of the prediction results PR regarding the success or failure of differentiation of cells for the respective imaging target ranges IR. In the example illustrated in FIG. 16, a ratio of the area for which differentiation is to be successful to the cell-culture area is about 26%.

Other Modifications

In the embodiment and modifications described above, the feature quantity extraction unit 53 extracts, as the feature quantity F, the number of cells or the increase rate in the number of cells out of the information related to the cell nuclei 31. The feature quantity extraction unit 53 may extract, as the feature quantity F, an area of the cell nucleus 31 (hereinafter, referred to as a nucleus area), an area ratio between the cell nucleus 31 and the cytoplasm 32 (hereinafter, referred to as an N/C ratio), or a proportion of a cell-occupied area (hereinafter, referred to as confluency) in the cell-culture container 25. Further, the feature quantity extraction unit 53 may extract, as the feature quantity F, circularity of the cell nucleus 31 (hereinafter, simply referred to as circularity).

FIG. 17 illustrates an example of relationships among various feature quantities F, an AUC, a sensitivity, and a specificity immediately before differentiation induction. The sensitivity is the true positive rate described above. The specificity is also referred to as the true negative rate. In FIG. 17, the "increase rate" is a value calculated on the basis of a plurality of captured images with different image-capturing times. In addition, "overall" represents an increase rate in a value determined for the entirety of the imaging region R. "Average" represents an average value in the entirety of the imaging region R. "Standard deviation" represents a degree of variation of the values in the entirety of the imaging region R.

In FIG. 17, various feature quantities F are arranged in descending order of AUC. FIG. 17 indicates that the increase rate in the number of cells (overall), the number of cells (average), the nucleus area (average), and the N/C ratio (average) have an AUD of 0.8 or greater, thus achieve a high determination accuracy, and are therefore preferable to be used as the feature quantity F for predicting differentiation of cells.

Figure 18:
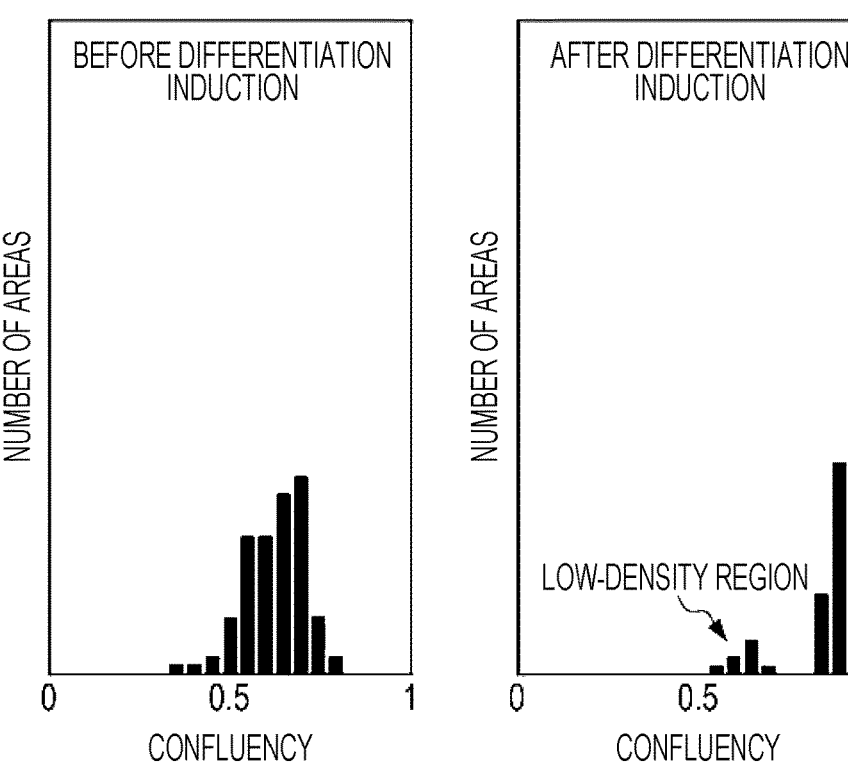
FIG. 18 depicts graphs illustrating frequency distributions of confluency before and after differentiation induction.
Figure 19:
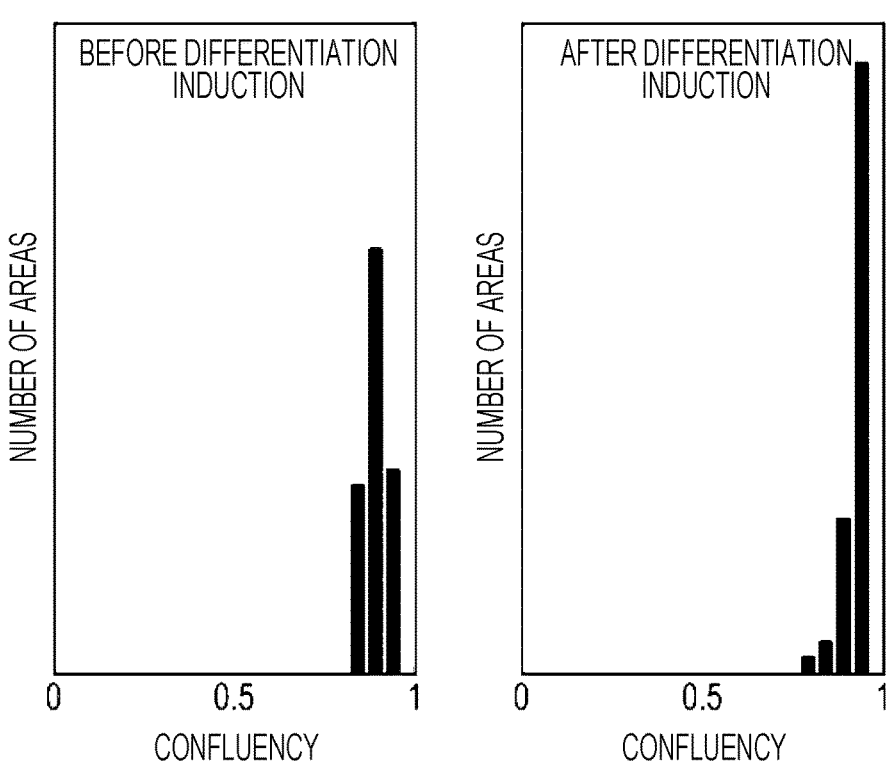
FIG. 19 depicts graphs illustrating frequency distributions of confluency before and after differentiation induction.

FIGS. 18 and 19 illustrate frequency distributions of the confluency before and after differentiation induction. FIG. 18 illustrates a comparison between the frequency distributions before and after differentiation induction in the case where the variation in the confluency is large before differentiation induction. FIG. 19 illustrates a comparison between the frequency distributions before and after differentiation induction in the case where the variation in the confluency is small before differentiation induction. In FIGS. 18 and 19, the vertical axis represents the number of regions (that is, the number of imaging target ranges IR).

As illustrated in FIG. 18, when the variation is large in the state before differentiation induction, the variation is also large in the state after differentiation induction, and a low-density region is partially is generated. In this low-density region, differentiation is highly likely to be unsuccessful. In contrast, as illustrated in FIG. 19, when the variation is small in the state before differentiation induction, the low-density region is not generated and differentiation is highly likely to be successful in the entire region.

As described above, FIGS. 18 and 19 indicate that differentiation of cells is predictable by using the variation (for example, the standard deviation) in the confluency as the feature quantity F.

Figure 20:
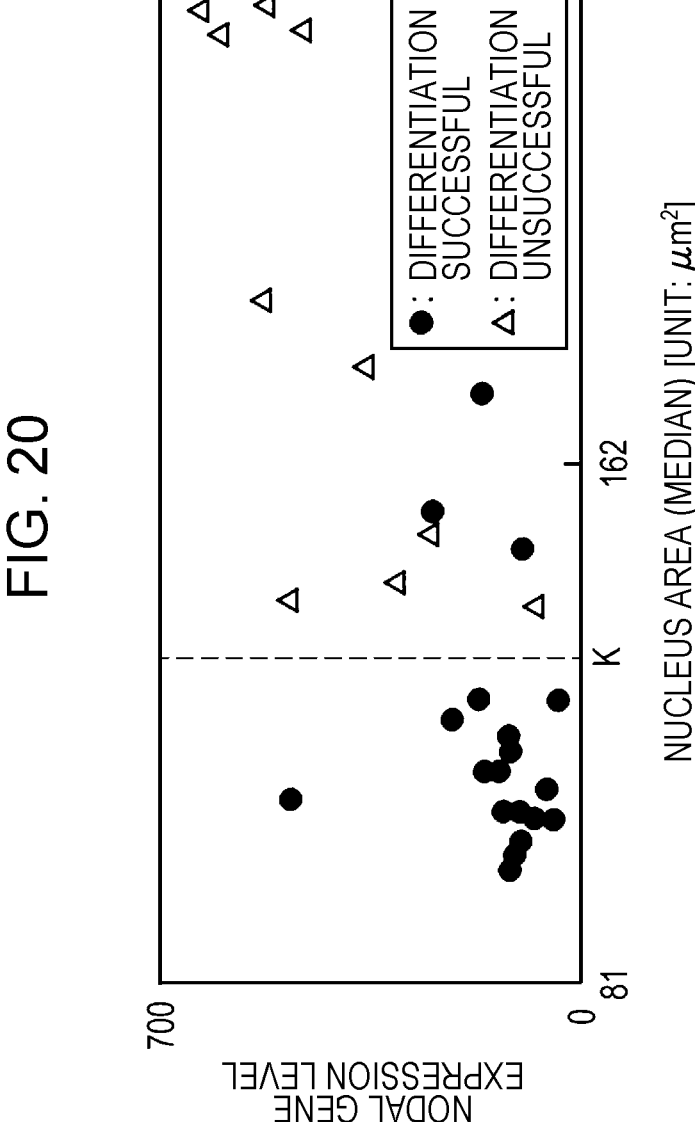
FIG. 20 is a diagram illustrating a relationship between an expression level of the Nodal gene and a nucleus area in the case where iPS cells are induced to differentiate into the cardiac muscle.

FIG. 20 illustrates a relationship between an expression level of the Nodal gene and the nucleus area in the case where iPS cells are induced to differentiate into the cardiac muscle. FIG. 20 illustrates results of an experiments for 29 batches (cell-culture containers 25). Black circles indicate batches for which differentiation is successful. White triangles indicate batches for which differentiation is unsuccessful. The Nodal gene is a marker that enables differentiation potency of iPS cells to differentiate into the cardiac muscle to be determined (see WO2020/203712A). Note that the expression level of the Nodal gene is a value measured using the targeted amplicon sequence method (in units of the number of counted pieces of data). In addition, the nucleus area means the area of the cell nucleus per cell.

FIG. 20 indicates that there is a correlation between the expression level of the Nodal gene and the nucleus area. By using the nucleus area as the feature quantity F and appropriately setting the determination criterion K, differentiation of cells can be accurately predicted. In the example illustrated in FIG. 20, differentiation of cells can be accurately predicted by setting K to about 142 μm². That is, if the nucleus area is about 142 μm² or less, it can be said that differentiation is likely to be successful. In the example illustrated in FIG. 20, a determined success rate of cells that successfully differentiate is 89.7%.

In the embodiment and modifications described above, the feature quantity extraction unit 53 extracts one type of feature quantity F (for example, the average number of cells) but may extract a plurality of types of feature quantities F (for example, the average number of cells, the average nucleus area, and the average N/C ratio). In this case, the prediction unit 54 may predict the success or failure of differentiation by performing multivariate analysis or the like by using the plurality of types of feature quantities F extracted by the feature quantity extraction unit 53.

In the embodiment and modifications described above, the cells 30 are pluripotent stem cells in an undifferentiated state, such as iPS cells and ES cells. However, the cells 30 may be stem cells in an undifferentiated state, such as mesenchymal stem cells.

The hardware configuration of the computer constituting the information processing apparatus 10 can be variously modified. For example, the information processing apparatus 10 may be constituted by a plurality of computers that are separated pieces of hardware for the purpose of increasing the processing capability and reliability.

As described above, the hardware configuration of the computer constituting the information processing apparatus 10 can be appropriately changed in accordance with the required performance such as the processing capability, the security, or the reliability. Further, not only the hardware but also the application programs such as the operation program 44 can be stored in a duplicated manner or stored in a plurality of storage devices in a distributed manner for the purpose of ensuring the security and the reliability.

In the embodiment described above, for example, various processors mentioned below can be used as a hardware structure of the processing units that perform various processes, such as the imaging control unit 50, the RW control unit 51, the processing unit 52, the feature quantity extraction unit 53, the prediction unit 54, and the display control unit 55. The various processors include, in addition to a CPU which is a general-purpose processor that executes software (the operation program 44) to function as the various processing units, a programmable logic device (PLD), such as a field programmable gate array (FPGA), which is a processor whose circuitry is changeable after production, a dedicated electric circuit, such as an application specific integrated circuit (ASIC), which is a processor having circuitry designed specifically for executing specific processing, and the like.

A single processing unit may be constituted by one of these various processors, or by a combination of two or more processors of the same kind or different kinds (for example, a combination of a plurality of FPGAs and/or a combination of a CPU and an FPGA). In addition, the plurality of processing units may be implemented by a single processor.

Examples in which the plurality of processing units are constituted by a single processor include a first configuration, as exemplified by computers such as a server and a client, in which a combination of one or more CPUs and software constitutes the single processor and this processor functions as the plurality of processing units. The examples also include a second configuration, as exemplified by a system on chip (SoC) or the like, in which a processor that implements functions of the entire system including the plurality of processing units on a single integrated circuit (IC) chip is used. As described above, the various processing units are constituted using one or more of the various processors above in terms of the hardware structure.

Further, as the hardware structure of these various processors, more specifically, electric circuitry in which circuit elements such as semiconductor elements are combined can be used.

In addition, the embodiment and modifications described above can be appropriately combined within a range in which no contradiction occurs.

All the documents, patent applications, and technical standards mentioned in this specification are incorporated herein by reference to the same extent as if the individual documents, patent applications, and technical standards were specifically and individually described to be incorporated by reference.

What is claimed is:

1. An information processing apparatus that predicts a success or failure of differentiation of cells on the basis of a captured image obtained by imaging a cell population cultured in a cell-culture container, the information processing apparatus comprising:

at least one processor configured to:

extract a feature quantity based on an appearance of the cells by performing image processing on the captured image;

predict the success or failure of differentiation of the cells by comparing the extracted feature quantity with a determination criterion stored in a storage device, and output a prediction result; and output an instruction for preventing a cell population predicted to have unsuccessful differentiation from being introduced into a differentiation induction process based on the prediction result, wherein the image processing includes:

inputting the captured image into a trained model to generate an output image in which pixels are classified into classes including a cell nucleus, cytoplasm, and a culture medium;

detecting cell nuclei from the output image based on a result of the classification; and extracting information related to the detected cell nuclei as the feature quantity.

2. The information processing apparatus according to claim 1, wherein the at least one processor is configured to predict the success or failure of differentiation of the cells on the basis of only the feature quantity based on the appearance of the cells.

3. The information processing apparatus according to claim 1, wherein the feature quantity includes a number of cells corresponding to a number of cell nuclei, an area of a cell nucleus, an area ratio between a cell nucleus and cytoplasm, or a proportion of a cell-occupied area in the cell-culture container.

4. The information processing apparatus according to claim 1, wherein the feature quantity includes an increase rate in a number of cells calculated on the basis of a plurality of captured images with different image-capturing times.

5. The information processing apparatus according to claim 1, wherein the at least one processor is configured to detect the cell nuclei from the captured image using a trained model obtained by performing machine learning using, as training data, a fluorescence image in which a cell nucleus is stained.

6. The information processing apparatus according to claim 1, wherein the at least one processor is configured to predict the success or failure of differentiation of the cells for each of a plurality of regions into which entirety of the cell-culture container is divided, by using, as the captured image, each of a plurality of region images obtained by imaging the plurality of regions.

7. The information processing apparatus according to claim 6, wherein the at least one processor is configured to calculate a ratio of an area for which differentiation is to be successful to a cell-culture area on the basis of prediction results about the success or failure of differentiation of the cells for the respective regions.

8. The information processing apparatus according to claim 1, wherein the cells are stem cells.

9. The information processing apparatus according to claim 8, wherein the stem cells are in an undifferentiated state.

10. An information processing method for predicting a success or failure of differentiation of cells on the basis of a captured image obtained by imaging a cell population cultured in a cell-culture container, the information processing method comprising:

extracting a feature quantity based on an appearance of the cells by performing image processing on the captured image;

predicting the success or failure of differentiation of the cells by comparing the extracted feature quantity with a determination criterion stored in a storage device, and outputting a prediction result; and outputting an instruction for preventing a cell population predicted to have unsuccessful differentiation from being introduced into a differentiation induction process based on the prediction result, wherein the image processing includes:

inputting the captured image into a trained model to generate an output image in which pixels are classified into classes including a cell nucleus, cytoplasm, and a culture medium;

detecting cell nuclei from the output image based on a result of the classification; and extracting information related to the detected cell nuclei as the feature quantity.

11. A non-transitory computer-readable storage medium storing a program for causing a computer to execute a process of predicting a success or failure of differentiation of cells on the basis of a captured image obtained by imaging a cell population cultured in a cell-culture container, the process comprising:

extracting a feature quantity based on an appearance of the cells by performing image processing on the captured image;

predicting the success or failure of differentiation of the cells by comparing the extracted feature quantity with a determination criterion stored in a storage device, and outputting a prediction result; and outputting an instruction for preventing a cell population predicted to have unsuccessful differentiation from being introduced into a differentiation induction process based on the prediction result, wherein the image processing includes:

inputting the captured image into a trained model to generate an output image in which pixels are classified into classes including a cell nucleus, cytoplasm, and a culture medium;

detecting cell nuclei from the output image based on a result of the classification; and extracting information related to the detected cell nuclei as the feature quantity.

12. An information processing apparatus that predicts a success or failure of differentiation of cells on the basis of a captured image obtained by imaging a cell population cultured in a cell-culture container, the information processing apparatus comprising:

at least one processor configured to:

extract a feature quantity based on an appearance of the cells by performing image processing on the captured image;

predict the success or failure of differentiation of the cells by comparing the extracted feature quantity with a determination criterion stored in a storage device, and output a prediction result; and output an instruction for preventing a cell population predicted to have unsuccessful differentiation from being introduced into a differentiation induction process based on the prediction result, wherein the image processing includes:

inputting the captured image into a trained model to generate an output image in which pixels are classified into classes including a cell nucleus, cytoplasm, and a culture medium; and extracting the feature quantity based on the output image, wherein the at least one processor is further configured to:

predict the success or failure of differentiation of the cells for each of a plurality of regions into which entirety of the cell-culture container is divided, by using, as the captured image, each of a plurality of region images obtained by imaging the plurality of regions; and calculate a ratio of an area for which differentiation is to be successful to a cell-culture area on the basis of prediction results about the success or failure of differentiation of the cells for the respective regions.

13. An information processing apparatus that predicts a success or failure of differentiation of cells on the basis of a captured image obtained by imaging a cell population cultured in a cell-culture container, the information processing apparatus comprising:

at least one processor configured to:

extract a feature quantity based on an appearance of the cells by performing image processing on the captured image;

predict the success or failure of differentiation of the cells by comparing the extracted feature quantity with a determination criterion stored in a storage device, and output a prediction result; and output an instruction for preventing a cell population predicted to have unsuccessful differentiation from being introduced into a differentiation induction process based on the prediction result, wherein the image processing includes:

inputting the captured image into a trained model to generate an output image in which pixels are classified into classes including a cell nucleus, cytoplasm, and a culture medium; and extracting the feature quantity based on the output image, wherein the cells are stem cells in an undifferentiated state.

14. An information processing method for predicting a success or failure of differentiation of cells on the basis of a captured image obtained by imaging a cell population cultured in a cell-culture container, the information processing method comprising:

extracting a feature quantity based on an appearance of the cells by performing image processing on the captured image;

predicting the success or failure of differentiation of the cells by comparing the extracted feature quantity with a determination criterion stored in a storage device, and outputting a prediction result; and outputting an instruction for preventing a cell population predicted to have unsuccessful differentiation from being introduced into a differentiation induction process based on the prediction result, wherein the image processing includes:

inputting the captured image into a trained model to generate an output image in which pixels are classified into classes including a cell nucleus, cytoplasm, and a culture medium; and extracting the feature quantity based on the output image, wherein the information processing method further comprises:

predicting the success or failure of differentiation of the cells for each of a plurality of regions into which entirety of the cell-culture container is divided, by using, as the captured image, each of a plurality of region images obtained by imaging the plurality of regions; and calculating a ratio of an area for which differentiation is to be successful to a cell-culture area on the basis of prediction results about the success or failure of differentiation of the cells for the respective regions.

15. An information processing method for predicting a success or failure of differentiation of cells on the basis of a captured image obtained by imaging a cell population cultured in a cell-culture container, the information processing method comprising:

extracting a feature quantity based on an appearance of the cells by performing image processing on the captured image;

predicting the success or failure of differentiation of the cells by comparing the extracted feature quantity with a determination criterion stored in a storage device, and outputting a prediction result; and outputting an instruction for preventing a cell population predicted to have unsuccessful differentiation from being introduced into a differentiation induction process based on the prediction result, wherein the image processing includes:

inputting the captured image into a trained model to generate an output image in which pixels are classified into classes including a cell nucleus, cytoplasm, and a culture medium; and extracting the feature quantity based on the output image, wherein the cells are stem cells in an undifferentiated state.

16. A non-transitory computer-readable storage medium storing a program for causing a computer to execute a process of predicting a success or failure of differentiation of cells on the basis of a captured image obtained by imaging a cell population cultured in a cell-culture container, the process comprising:

extracting a feature quantity based on an appearance of the cells by performing image processing on the captured image;

predicting the success or failure of differentiation of the cells by comparing the extracted feature quantity with a determination criterion stored in a storage device, and outputting a prediction result; and outputting an instruction for preventing a cell population predicted to have unsuccessful differentiation from being introduced into a differentiation induction process based on the prediction result, wherein the image processing includes:

inputting the captured image into a trained model to generate an output image in which pixels are classified into classes including a cell nucleus, cytoplasm, and a culture medium; and extracting the feature quantity based on the output image, wherein the process further comprises:

predicting the success or failure of differentiation of the cells for each of a plurality of regions into which entirety of the cell-culture container is divided, by using, as the captured image, each of a plurality of region images obtained by imaging the plurality of regions; and calculating a ratio of an area for which differentiation is to be successful to a cell-culture area on the basis of prediction results about the success or failure of differentiation of the cells for the respective regions.

17. A non-transitory computer-readable storage medium storing a program for causing a computer to execute a process of predicting a success or failure of differentiation of cells on the basis of a captured image obtained by imaging a cell population cultured in a cell-culture container, the process comprising:

extracting a feature quantity based on an appearance of the cells by performing image processing on the captured image;

predicting the success or failure of differentiation of the cells by comparing the extracted feature quantity with a determination criterion stored in a storage device, and outputting a prediction result; and outputting an instruction for preventing a cell population predicted to have unsuccessful differentiation from being introduced into a differentiation induction process based on the prediction result, wherein the image processing includes:

inputting the captured image into a trained model to generate an output image in which pixels are classified into classes including a cell nucleus, cytoplasm, and a culture medium; and extracting the feature quantity based on the output image, wherein the cells are stem cells in an undifferentiated state.

* * * * *